(12) United States Patent
Wening et al.

(10) Patent No.: US 9,855,263 B2
(45) Date of Patent: *Jan. 2, 2018

(54) TAMPER-RESISTANT DOSAGE FORM WITH IMMEDIATE RELEASE AND RESISTANCE AGAINST SOLVENT EXTRACTION

(71) Applicant: GRÜNENTHAL GMBH, Aachen (DE)

(72) Inventors: Klaus Wening, Köln (DE); Anja Geißler, Karlsruhe (DE); Jana Denker, Bornheim (DE); Lutz Barnscheid, Mönchengladbach (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/169,778

(22) Filed: Jun. 1, 2016

(65) Prior Publication Data

US 2016/0310487 A1   Oct. 27, 2016

Related U.S. Application Data

(63) Continuation of application No. 15/135,649, filed on Apr. 22, 2016, now abandoned.

(30) Foreign Application Priority Data

Apr. 24, 2015 (EP) .................................... 15165064

(51) Int. Cl.
| | | |
|---|---|---|
| A61K 9/50 | (2006.01) | |
| A61K 31/485 | (2006.01) | |
| A61K 9/16 | (2006.01) | |
| A61K 9/20 | (2006.01) | |
| A61K 9/48 | (2006.01) | |
| A61K 31/137 | (2006.01) | |

(52) U.S. Cl.
CPC .......... *A61K 31/485* (2013.01); *A61K 9/1611* (2013.01); *A61K 9/1617* (2013.01); *A61K 9/1635* (2013.01); *A61K 9/1641* (2013.01); *A61K 9/1652* (2013.01); *A61K 9/1658* (2013.01); *A61K 9/1694* (2013.01); *A61K 9/2077* (2013.01); *A61K 9/4808* (2013.01); *A61K 9/50* (2013.01); *A61K 31/137* (2013.01)

(58) Field of Classification Search
CPC ...... A61K 31/135; A61K 4/10; A61K 31/137; A61K 31/485; A61K 9/1611; A61K 9/1617; A61K 9/1635; A61K 9/1641; A61K 9/1652; A61K 9/1658; A61K 9/1694; A61K 9/2077; A61K 9/4808; A61K 9/50; C08G 63/66
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |

(Continued)

FOREIGN PATENT DOCUMENTS

| | | |
|---|---|---|
| AR | 046994 A1 | 12/2004 |
| AR | 045353 A1 | 10/2005 |

(Continued)

OTHER PUBLICATIONS

Tennant (Simultaneous Use of Stimulants and Opioids, 2011. [online] retrieved on Jul. 7, 2016 from: http://www.practicalpainmanagement.com/treatments/pharmacological/opioids/simultaneous-use-stimulants-opioids; 7 pages.*
Starch 1500 technical data from Colorcon 2016 6 pages.*
Fathima et al. (JAPS 2011;01(06):66-71).*
Alekseeva et al, Chemical-Pharmaceutical Journal, vol. 41, No. 9, 2007, 49-52. (Full translation attached.)
2.9 Methoden der pharmazeutischen Technologie, European Pharmacopeia, 143-144, 1997. (Full English translation attached).
Albertini, B. "New spray congealing atomizer for the microencapsulation of highly concentrated solid and liquid substances" European Journal of Pharmaceutics and Biopharmaceutics 69 (2008) 348-357.
Alekseeva et al, Chemical-Pharmaceutical Journal, vol. 41, No. 9, 2007, 49-52. (English abstract included.).

(Continued)

*Primary Examiner* — Ernst V Arnold
(74) *Attorney, Agent, or Firm* — Norris McLaughlin & Marcus, P.A.

(57) ABSTRACT

A tamper-resistant pharmaceutical dosage form comprising a multitude of particles which comprise a pharmacologically active compound, a polyalkylene oxide, and a disintegrant; wherein the pharmacologically active compound is dispersed in a matrix comprising the polyalkylene oxide and the disintegrant; wherein the content of the disintegrant is more than 5.0 wt.-%, based on the total weight of the pharmaceutical dosage form and/or based on the total weight of the particles; wherein the content of the polyalkylene oxide is at least 25 wt.-%, based on the total weight of the pharmaceutical dosage form and/or based on the total weight of the particles; and wherein the dosage form provides under in vitro conditions immediate release of the pharmacologically active compound in accordance with Ph. Eur.

21 Claims, 4 Drawing Sheets

(56) References Cited

U.S. PATENT DOCUMENTS

| | | |
|---|---|---|
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | LaHann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Graudums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merrill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breitenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |

(56) References Cited

U.S. PATENT DOCUMENTS

| | | |
|---|---|---|
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 9,192,578 B2 | 11/2015 | McGinity et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara et al. |
| 2004/0213848 A1 | 10/2004 | Li et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0240105 A1 | 10/2006 | DeVane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |

(56) References Cited

U.S. PATENT DOCUMENTS

| | | |
|---|---|---|
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2009/0318395 A1 | 12/2009 | Schramm et al. |
| 2010/0015223 A1 | 1/2010 | Cailly-Deufestel et al. |
| 2010/0035886 A1* | 2/2010 | Cincotta .............. A61K 9/0019 514/250 |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Andersen et al. |
| 2011/0187017 A1 | 8/2011 | Haupts |
| 2011/0245783 A1 | 10/2011 | Stinchcomb et al. |
| 2011/0262496 A1* | 10/2011 | Desai .................. A61K 31/135 424/400 |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0090349 A1 | 4/2013 | Geiβer et al. |
| 2013/0129825 A1 | 5/2013 | Billoet et al. |
| 2013/0129826 A1 | 5/2013 | Geiβer et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau-Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |

FOREIGN PATENT DOCUMENTS

| | | |
|---|---|---|
| AR | 049562 A1 | 8/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |

(56) References Cited

FOREIGN PATENT DOCUMENTS

| | | |
|---|---|---|
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 | 5/2005 |
| CL | 200403308 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 9/2008 |
| CN | 101370485 A | 2/2009 |
| CN | 101394839 A | 3/2009 |
| CN | 101652128 A | 2/2010 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |

(56) References Cited

FOREIGN PATENT DOCUMENTS

| | | |
|---|---|---|
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | 2002524150 A | 8/2002 |
| JP | 2002-275175 A | 9/2002 |
| JP | 2003125706 A | 5/2003 |
| JP | 2003526598 A | 9/2003 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2011504455 A | 2/2011 |
| JP | 2011506493 A | 3/2011 |
| JP | 2013536810 A | 9/2013 |
| JP | 2014505736 A | 3/2014 |
| JP | 2014528437 A | 10/2014 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026262 A1 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/013433 A2 | 2/2003 |

(56) References Cited

FOREIGN PATENT DOCUMENTS

| | | |
|---|---|---|
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 A1 | 7/2015 |

OTHER PUBLICATIONS

Almeida, A. et al., Ethylene vinyl acetate as matrix for oral sustained release dosage forms produced via hot-melt extrusion, European Journal of Pharmaceutics and Biopharmaceutics 77 (2011) 297-305.

(56) References Cited

OTHER PUBLICATIONS

Almeida, A. et al., Sustained release from hot-melt extruded matrices based on ethylene vinyl acetate and polyethylene oxide, European Journal of Pharmaceutics and Biopharmaceutics 82 (2012) 526-533.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90,1993.
Application of a modelling system in the formulation of extended release hydrophilic matrices, Reprinted from Pharmaceutical Technology Europe, Jul. 2006.
Application of Opadry II, complete film coating system, on metformin HCI extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., Catalytic Hydrogenation of a, B-Unsaturated Ketones. III The Effect of Quantity and Type of Catalysts, J.Org Chem. 28(1), pp. 152-155, Abstract 1963.
Avis, Kenneth, Parenteral Preparations. Chapter 85. pp. 1518-1541In Remington's Pharmaceutical Pharmaceutical Sciences, 17th Ed, 1985.
Bailey, F.E., et al., "Some properties of polyethylene oxide)' in aqueous solution," Journal of Applied Polymer Science, vol. 1, Issue No. 1, pp. 56-62, 1959.
Bauer et al. Lehrbuch der Pharmazeutischen Technologie. Eight Edition 2006. Stuttgart, pp. 343-352.
Bauer et al. Lehrbuch der Pharmazeutischen Technologie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug. 1987, vol. 102, No. 4, p. 426-429.
Bingwen et al, 2008, p. 367. (full translation attached).
Block, Lawrence. Medicated Applications. Chapter 88. In Remington's Pharmaceutical Sciences, 17th Ed, 1985.
Borquist et al., "Simulation of the release from a multiparticulate system validated by single pellet and dose release experiements," J. Controlled Release, 97: 453-465 (2004).
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Bruce et al, Properties of hot-melt extuded tablet formulations for the colonic delivery of 5-aminosalicylic acid, European Journal of Pharmaceutics and Biopharmaceutics, 59 (2005) 85-97.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Committee for Proprietary Medicinal Products. Note for Guidance on the Investigation of Bioavailability and Bioequivalence. 2001. pp. 1-18.

Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia ora feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-melt extrusion," Biomaterials 23, 2002, pp. 4241-4248.
Crowley MM, Drug Dev Ind Pharm. Sep. 2007; 33(9):909-26. (Abstract only).
Cuesov, 1999, pp. 351-352.
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med, vol. 93, 2000, pp. 29-33.
DeJong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, POLYOX WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.

(56) References Cited

OTHER PUBLICATIONS

Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83. pp. 1487-1491 In Remington's Pharmaceutical Sciences, 17th Ed, 1985.
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708.1.-1219, dated Sep. 24, 2012.
European Search Report and Opinion Application No. 14176277.3-1460, dated Dec. 15, 2014.
European Search Report and Opinion, Application No. 11006253.6-2112, dated Dec. 16, 2011.
European Search Report and Opinion, Application No. 11006254.4-2112, dated Dec. 16, 2011.
European Search Report and Opinion, Application No. 11008131.2-1219, dated Feb. 24, 2012.
European Search Report and Opinion, Application No. 11009129.5-2112, dated Apr. 10, 2012.
European Search Report and Opinion, Application No. 12001296.8-1219, dated Jun. 26, 2012.
European Search Report and Opinion, Application No. 12001301.6-1219, dated Jun. 26, 2012.
European Search Report and Opinion, Application No. 12003743.7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
European Search Report and Written Opinion for EP Application No. 14169801.9-1455 dated Oct. 20, 2014.
Evaluation of Verapamil HCI (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: EUDRAGIT acrylic polymers for solid oral dosage forms (2009).
Extended European Search Report and Opinion for Application No. EP 15153679.4-1455, dated Jun. 30, 2015.
Extended European Search Report and Opinion for Application No. EP 15165064.5-1455, dated Oct. 16, 2015.
Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.
Extended European Search Report and Opinion for Application No. EP 15184634.2-1455, dated Mar. 3, 2016.
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N. B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCI 500mg Extended Release Formulation Based on Hypromellose, Colorcon Jul. 2009.

(56) References Cited

OTHER PUBLICATIONS

James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
King, Remington's Pharmaceutical Sciences 17th ed., Chapter 78, p. 1418 (1985).
Knevel, Adelbert. Separation. Chapter 78. pp. 1432-1442 In Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Lee, Y.-S. et al., Principles of Terahertz Science and Technology (Lecture Notes in Physics), Springer; 1 edition 2008. (Table of Contents Only).
Lenindzer, A., "The molecular basis of the structure and functions of cells" Moscow 1974, p. 68.
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. Volume 2 (Cover and Table of Content only).
Lintner, Carl. Stability of Pharmaceutical Products. Chapter 82. pp. 1478-1486 In Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional; First Edition 1996. (Table of contents only).
Longer et al. Sustained-Release Drug Delivery Systems. Chapter 92. pp. 1611-1661 in Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstofflliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises á jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Monolithic: retrieved from internet: http:/merriam-webster.com/dictionary/monolithic. Retrieved on Sep. 2, 2015.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.
Moroni A. et al, "Application of Poly(Oxyethylene) Homopolymers in Sustained release Solid Formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta[79] 9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.

(56) References Cited

OTHER PUBLICATIONS

Oxicotin: Balancing Risks and Benefits, United States Senate, Hearing, Feb. 12, 2002.
Oxycodon (Oxygesic): Missbrauch, Abhaengigkeit and toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene oxide)—Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)"Journal of Controlled Release 58, pp. 87-95, 1999.
PCT International Search Report and Written Opinion for PCT Application No. PCT/EP2009/003290 dated Jul. 9, 2009.
PCT International Search Report and Written Opinion for PCT Application No. PCT/EP2010/004459 dated Dec. 1, 2010.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Oct. 1991, 8(10), S-192.
Pharm. Research, Official Journal of the American Association of Pharmaceutical Scientists, Sep. 1989, 6(9), S-98.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
Polyox water-soluble resins (Dow Mar. 2002); see http://msds-search.dow.com/PublishedLiteratureDOWCOM/dh_0031/0901b8038003 1a4a.pdf?filepath=/326-00001.pdf &fromPage=GetDoc).
Polyox WSR-303, retrieved Mar. 10, 2014 from URL http://www.dow.com/dowwolff/en/industrial_solutions/polymers/polyethylene.
Polyox, Colorcon, Application Data (Apr. 2009) downloaded from http://www.colorcon.com/literature/marketing/mr/Extended %20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain edications; FDA Cites Patient Needs as First Priority; New Drug Application Delayed," www.headaches.about.com, Jun. 18, 2002, pp. 1-6.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka Ma, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Bioharmaceutics, vol. 85, No. 3, (Jul. 25, 2013). pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Saleem et al. "Formulation and Evaluation of Tramadol hydrochloride Rectal Suppositories," Indian J. Pharm Sci. Sep.-Oct. 2008; 70(5), 640-644.

(56) References Cited

OTHER PUBLICATIONS

Salomies et al., "Determination of Oxycodone Hydrochloride in Oral Solutions by High-Performance Thin-Layer Chromatography/Densitometry," Journal of AOAC International, 83: 1497-1501 (2000).
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/new-tons-to-kiloponds-convresion.html, on Jul. 5, 2011 (Conversion of 18.8 kiloponds to newtons).
Shivanand P. et al., "Factors Affecting Release of KCI From Melt extruded Polyethylene Disks", Pharmaceutical Research, Oct. 1991, vol. 8, No. 10, p. S-192.
Sidhu et al., "Watch for nonpsychotropics causing psychiatric side effects," Current Psychiatry, vol. 7, No. 4, 2008, 61-74.
Siegel, P. Tonicity, Osmoticity, Osmolality, and Osmolarity. Chapter 80. pp. 1454-1472 In Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., überzogene feste Formen, 1991, 347-68. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked of ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Vippagunta et al. Crystalline Solids, Advanced Drug Delivery Review 48 (2001), 3-26.
Vynckier et al., "Hot-melt co-extrusion for the production of fixed-dose combination products with a controlled release ethylcellulose matrix core," International Journal of Pharmaceutics 464 (2014), 65-74.
Wade and Weller, "Handbook of Pharmaceutical Excipients: 2nd Edition", The American Pharmaceutical Association and the Pharmaceutical Press, Washington and London, Table of Contents pp. v-vi, 1994.

(56) References Cited

OTHER PUBLICATIONS

Wagner, Pharmazeutische Biologie—Drogen und ihre Inhaltsstoffe—Scharfstoffdrogen, 2nd., revised edition, Gustav Fischer Verlag, Stuttgart-N.Y., 1982, pp. 82-92 (Full English translation attached).
Wagner, Pharmazeutische Biologie—Drogen und ihre Inhaltsstoffe—Scharfstoffdrogen, 2nd., revised edition, Gustav Fischer Verlag, Stuttgart-N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", *Acta Odontol Scand* 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U., "Derivatives of Morphine. I 14-Dihydroxydihydromorphinone," J. Am. Chem. Soc. 77, pp. 5891-5892, Nov. 20, 1955.
West, Anthony R., Solid state chemistry and its applications, Wiley, New York, 1988, pp. 358 and 365.
Wikipedia-Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar- and -pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmSciTech 11(2); 910-916 (available on-line May 22, 2010).
Zhang et al., "Properties of Sustained-Release Tablets Prepared by Hot-Melt Extrusion" Pharmaceutical Develoftment and Technology, 1999, 4(2), 241-250.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Decision of the United States District Court for the Southern District of New York, in In re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14 2014.
Decision of the United States District Court for the Southern District of New York, in In re *Oxycontin Antitrust Litigation, Purdue Pharma LP* v. *Teva Phamaceuticals*, Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117 USPQ2d 1733 (Fed. Cir. 2016).

Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization. In Polystyrene," Macromolecules 28:2944-54 (1995).
Back, D.M.et al., "Ethylene Oxide Polymers", in Kirk-Othmer Encyclopedia of Chemical Technolpgy. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in a Tastes of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the $29^{th}$ Annual Meeting of the Controlled Release Society, in collaboration with the Korea Society for Biomaterials, Minneapolis, $1^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002). Controversies in ADHD: A Breakfast Symposium—Concerta.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of The University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
Crowley0000001-Crowley0000127.
Davies, N. "Sustained Release and Enteric Coated NSAIDs: Are They Really GI Safe?" J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun., 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.

(56) References Cited

OTHER PUBLICATIONS

FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts at Intranasal Abuse of Concerta," Letters to the Editor, J. Am. Acad. Child Adolesc. Psychiatry, 41:1 (Jan. 2002).
Jannsen Pharmaceuticals, Inc. Concerta Labeling Revisions, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al. ,"Properties of Tablets Containing Granulations of Ibuprofen and Acrylic Copolymers Prepared by Thermal Processes," Pharm Dev, and Tech. , 6:263-275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int 'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms" in Pharmaceutical Extrustion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Statue Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int 'l J. Pharmaceutics (1996) 138:215-224.
National Drug Intelligence Center Information Bulletin "OxyContin Diversion and Abuse" Jan. 2001.

Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and disintegration of paracetamol and oxytetracylcine tablets," J Pharm Pharmac., 29:389-392 (1977).
POLYOX Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version Sep. 10, 2016; available at www.purduephruma.com/msdss/oxycontin_msds.pdf.
Rauwendaal, Chris, PHD, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compressed Tablets 1: Tablet Hardnessand Friability," J. of Pharrn. Sci. , 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5. 2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide in Rubber-Like State." Journal of Physical Chemistry, 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
USP Expert Council, US Pharmacopoeia, Chapter 1092, 2007, 1-15.
M. Xu et al., "Evaluation of the coat quality of sustained release pellets by individual pellet dissolution methodology," Int. J. Pharm. 478 (2015) 318-327.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Cuesov, Drug Production Technology, Khar'kov, 1999, pp. 351-352. (Full translation attached.).
Efentakis et al, Effects of Excipients on Swelling and Drug Release from Compressed Matrices, in Drug Development and Industrial Pharmacy 23(1):107-112, Jan. 1997, Abstract.
Extended European Search Report for Application No. EP 16183922.0-1460, dated Oct. 31, 2016.
Koziolek, M. et al., "Development of a bio-relevant dissolution test device simulating mechanical aspects present in the fed stomach," European Journal of Pharmaceutical Sciences 57 (2014) 250-256.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.

(56) References Cited

OTHER PUBLICATIONS

Remington, Chapter 45, pp. 996-1035. (Full Translation Attached).
Schilling, et al., "Novel application of hot-melt extrusion for the preparation of monolithic matrices containing enteric-coated particles." International Journal of Pharmaceutics 400 (2010) 34-31.
Dabbagh, et al. "Release of Propranolol Hydrochloride from Matrix Tablets Containing Sodium Carboxymethylcellulose and Hydroxypropylmethylcelluloseu"; 1999; Pharmaceutical Development and Technology, 4(3), 313-324.
COMPAP 90 technical data sheet Mar. 2014; 1 page.

\* cited by examiner

TAMPER-RESISTANT DOSAGE FORM WITH IMMEDIATE RELEASE AND RESISTANCE AGAINST SOLVENT EXTRACTION

This application is a continuation of U.S. Nonprovisional application Ser. No. 15/135,649, filed Apr. 22, 2016, which, in turn, claims priority of European Patent Application No. 15 165 064.5, filed on Apr. 24, 2015, the entire contents of which patent applications are incorporated herein by reference.

The invention relates to a tamper-resistant pharmaceutical dosage form comprising a multitude of particles which comprise a pharmacologically active compound, a polyalkylene oxide, and a disintegrant; wherein the pharmacologically active compound is dispersed in a matrix comprising the polyalkylene oxide and the disintegrant; wherein the content of the disintegrant is more than 5.0 wt.-%, based on the total weight of the pharmaceutical dosage form and/or based on the total weight of the particles; wherein the content of the polyalkylene oxide is at least 25 wt.-%, based on the total weight of the pharmaceutical dosage form and/or based on the total weight of the particles; and wherein the dosage form provides under in vitro conditions immediate release of the pharmacologically active compound in accordance with Ph. Eur.

A large number of pharmacologically active substances have a potential for being abused or misused, i.e. they can be used to produce effects which are not consistent with their intended use. Thus, e.g. opioids which exhibit an excellent efficacy in controlling severe to extremely severe pain, are frequently abused to induce euphoric states similar to being intoxicated. In particular, active substances which have a psychotropic effect are abused accordingly.

To enable abuse, the corresponding dosage forms, such as tablets or capsules are crushed, for example ground by the abuser, the active substance is extracted from the thus obtained powder using a preferably aqueous liquid and after being optionally filtered through cotton wool or cellulose wadding, the resultant solution is administered parenterally, in particular intravenously. This type of dosage results in an even faster diffusion of the active substance compared to the oral abuse, with the result desired by the abuser, namely the kick. This kick or these intoxication-like, euphoric states are also reached if the powdered dosage form is administered nasally, i.e. is sniffed.

Various concepts for the avoidance of drug abuse have been developed.

It has been proposed to incorporate in dosage forms aversive agents and/or antagonists in a manner so that they only produce their aversive and/or antagonizing effects when the dosage forms are tampered with. However, the presence of such aversive agents is principally not desirable and there is a need to provide sufficient tamper-resistance without relying on aversive agents and/or antagonists.

Another concept to prevent abuse relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded. Thus, the pulverization, necessary for abuse, of the dosage forms by the means usually available to a potential abuser is prevented or at least complicated.

Such pharmaceutical dosage forms are useful for avoiding drug abuse of the pharmacologically active compound contained therein, as they may not be powdered by conventional means and thus, cannot be administered in powdered form, e.g. nasally. The mechanical properties, particularly the high breaking strength of these pharmaceutical dosage forms renders them tamper-resistant. In the context of such tamper-resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, and WO2009/092601.

These dosage forms secured against abuse are distinguished by a controlled, preferably retarded release of the active substance which has abuse potential. However, a rapid release of the active substance is necessary for numerous therapeutic applications, for example pain relief using active substances with abuse potential.

WO 2008/033523 discloses a pharmaceutical composition that may include a granulate which may at least include one active pharmaceutical ingredient susceptible to abuse. The particle contains both an alcohol soluble and alcohol insoluble and at least partially water soluble material. Both materials are granulated in the presence of alcohol and water. The granulate may also include a coating on the granulate exhibiting crush resistance. Material deposition on the granule is performed using an alcohol based solvent.

WO 2008/107149 (US 2009/004267) discloses multiparticulate dosage forms with impeded abuse containing, one or more active substances having abuse potential, at least one synthetic or natural polymer, and at least one disintegrant, with the individual particles of the pharmaceutical dosage form having a breaking strength of at least 500 N and a release of the active substance of at least 75% after 45 minutes. The exemplified capsules provide rapid release of the pharmacologically active compound. The disintegrant is preferably not contained in the particulates. When it is contained in the particulates, its content is rather low. The reference does not contain any information that besides its disintegrating effect a disintegrant may have any beneficial effect with respect to tamper resistance such as resistance against solvent extraction.

WO 2010/140007 discloses dosage forms comprising melt-extruded particles comprising a drug, wherein said melt-extruded particles are present as a discontinuous phase in a matrix. The dosage forms provide prolonged release of the drug.

WO 2013/017242 and WO 2013/017234 disclose a tamper-resistant tablet comprising a matrix material in an amount of more than one third of the total weight of the tablet; and a plurality of particulates in an amount of less than two thirds of the total weight of the tablet; wherein said particulates comprise a pharmacologically active compound and a polyalkylene oxide; and form a discontinuous phase within the matrix material. The matrix material may comprise a disintegrant. The reference does not contain any information that besides its disintegrating effect a disintegrant may have any beneficial effect with respect to tamper resistance such as resistance against solvent extraction.

WO2014/190440 relates to an immediate release orally administrable abuse-deterrent pharmaceutical formulation comprising: at least one pharmaceutically active ingredient susceptible to abuse; at least one gelling polymeric compound selected from the group consisting of: polysaccharides, sugars, sugar derived alcohols, starches, starch derivatives, cellulose derivatives, Carrageenan, pectin, sodium alginate, gellan gum, xanthan gum, poloxamer, carbopol, polyox, povidone, hydroxypropyl methylcellulose, hypermellose, and combinations thereof; at least one disintegrant and optionally at least one surfactant, wherein said formulation exhibit properties related to deterring the abuse, via injection or nasal inhalation when being tampered and exposed to aqueous, alcoholic, acidic and basic media.

US 2010/0092553 discloses solid multiparticle oral pharmaceutical forms whose composition and structure make it possible to avoid misuse. The microparticles have an extremely thick coating layer which assures the modified release of the drug and simultaneously imparts crushing resistance to the coated microparticles so as to avoid misuse.

The properties of these tamper-resistant dosage forms, however, are not satisfactory in every respect. There is a need for tamper-resistant dosage forms that possess crush resistance and release the pharmacologically active compound as quick as possible (immediate release), i.e. should show a gradual increase reaching 85% to 100% at 30 to 45 minutes or earlier. When trying to tamper the dosage form in order to prepare a formulation suitable for abuse by intravenous administration, the liquid part of the formulation that can be separated from the remainder by means of a syringe should be as less as possible, e.g. should contain not more than 10 wt.-% of the pharmacologically active compound originally contained in the dosage form.

It is an object according to the invention to provide tamper-resistant pharmaceutical dosage forms that provide rapid release of the pharmacologically active compound and that have advantages compared to the tamper-resistant pharmaceutical dosage forms of the prior art.

This object has been achieved by the patent claims.

The invention relates to a tamper-resistant pharmaceutical dosage form, preferably for oral administration, comprising a multitude of particles which comprise a pharmacologically active compound, a polyalkylene oxide, and a disintegrant; wherein the pharmacologically active compound is dispersed in a matrix comprising the polyalkylene oxide and the disintegrant; wherein the content of the disintegrant is more than 5.0 wt.-%, based on the total weight of the pharmaceutical dosage form and/or based on the total weight of the particles; wherein the content of the polyalkylene oxide is at least 25 wt.-%, based on the total weight of the pharmaceutical dosage form and/or based on the total weight of the particles; and wherein the dosage form provides under in vitro conditions immediate release of the pharmacologically active compound in accordance with Ph. Eur.

It has been surprisingly found that tamper-resistant dosage forms can be provided that on the one hand provide immediate release of the pharmacologically active compound and that on the other hand provide improved tamper-resistance, particularly with respect to resistance against solvent extraction.

Figure 1:
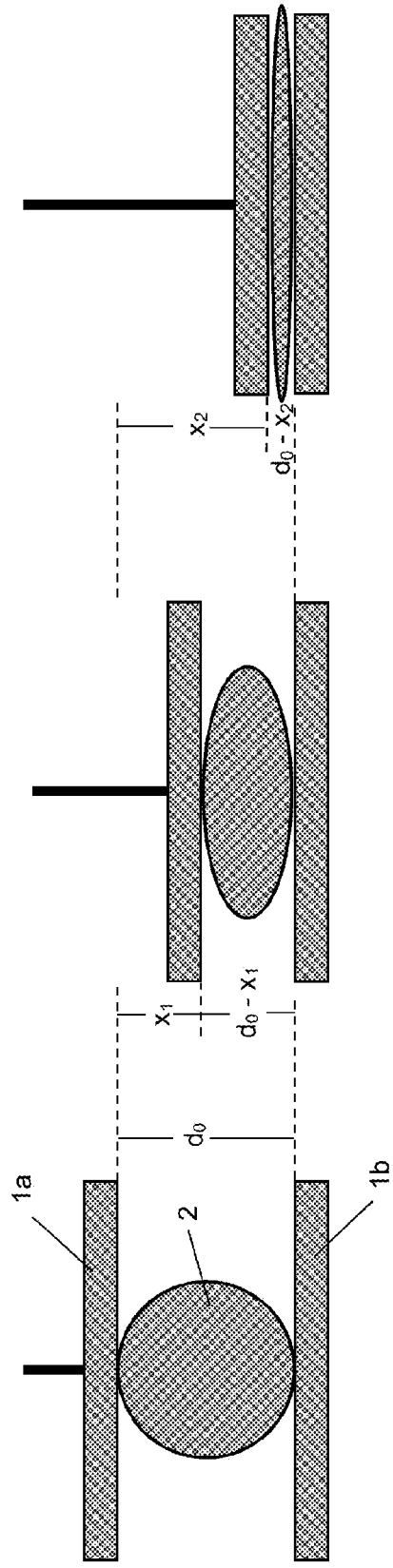
FIG. 1 illustrates the behavior of the particles contained in the pharmaceutical dosage form according to the invention when being subjected to a breaking strength test, in particular their deformability.
Figure 1:
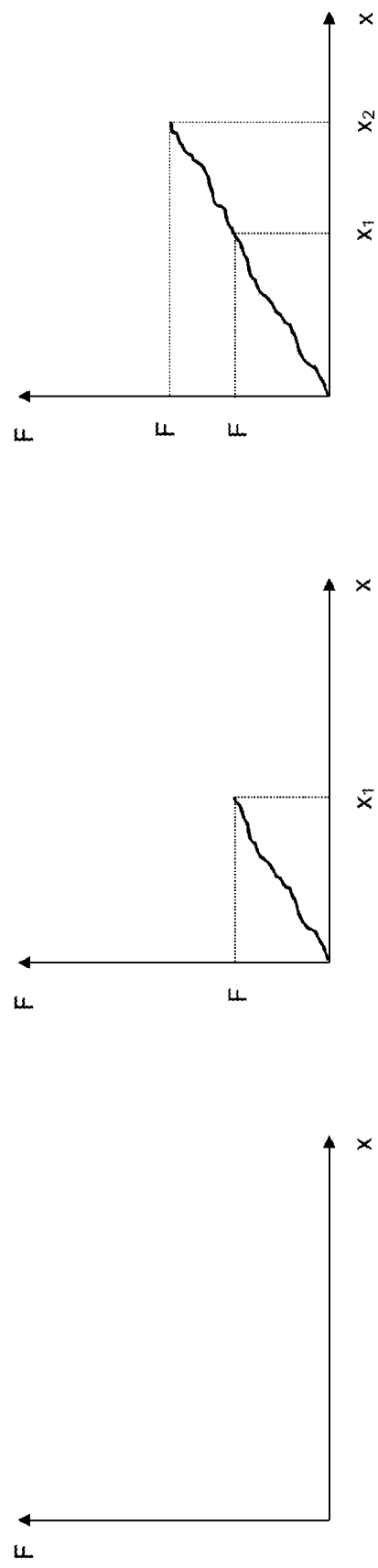

As used herein, the term "pharmaceutical dosage form" refers to a pharmaceutical entity comprising a pharmacologically active compound and which is actually administered to, or taken by, a patient, preferably orally.

Preferably, the pharmaceutical dosage from according to the invention is a capsule or a tablet. The particles that are contained in the pharmaceutical dosage form and/or the pharmaceutical dosage form as such may be film-coated.

The pharmaceutical dosage form may be compressed or molded in its manufacture, and it may be of almost any size, shape, weight, and color. Most pharmaceutical dosage forms are intended to be swallowed as a whole and accordingly, preferred pharmaceutical dosage forms according to the invention are designed for oral administration. However, alternatively pharmaceutical dosage forms may be dissolved in the mouth, chewed, or dissolved or dispersed in liquid or meal before swallowing, and some may be placed in a body cavity. Thus, the pharmaceutical dosage form according to the invention may alternatively be adapted for buccal, lingual, rectal or vaginal administration. Implants are also possible.

In a preferred embodiment, the pharmaceutical dosage form according to the invention preferably can be regarded as a MUPS formulation (multiple unit pellet system). In a preferred embodiment, the pharmaceutical dosage form according to the invention is monolithic. In another preferred embodiment, the pharmaceutical dosage form according to the invention is not monolithic. In this regard, monolithic preferably means that the pharmaceutical dosage form is formed or composed of material without joints or seams or consists of or constitutes a single unit.

In a preferred embodiment, the pharmaceutical dosage form according to the invention contains all ingredients in a dense compact unit which in comparison to capsules has a comparatively high density. In another preferred embodiment, the pharmaceutical dosage form according to the invention contains all ingredients in a capsule which in comparison to dense compact unit has a comparatively low density.

An advantage of the pharmaceutical dosage forms according to the invention is that the same particles may be mixed with excipients in different amounts to thereby produce pharmaceutical dosage forms of different strengths. Another advantage of the pharmaceutical dosage forms according to the invention is that the different particles may be mixed with one another to thereby produce pharmaceutical dosage forms of different properties, e.g. different release rates, different pharmacologically active ingredients, and the like.

The pharmaceutical dosage form according to the invention has preferably a total weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.3 g to 0.8 g. In a preferred embodiment, the total weight of the pharmaceutical dosage form is within the range of 500±450 mg, more preferably 500±300 mg, still more preferably 500±200 mg, yet more preferably 500±150 mg, most preferably 500±100 mg, and in particular 500±50 mg. In another preferred embodiment, the total weight of the pharmaceutical dosage form is within the range of 600±450 mg, more preferably 600±300 mg, still more preferably 600±200 mg, yet more preferably 600±150 mg, most preferably 600±100 mg, and in particular 600±50 mg. In still another preferred embodiment, the total weight of the pharmaceutical dosage form is within the range of 700±450 mg, more preferably 700±300 mg, still more preferably 700±200 mg, yet more preferably 700±150 mg, most preferably 700±100 mg, and in particular 700±50 mg. In yet another preferred embodiment, the total weight of the pharmaceutical dosage form is within the range of 800±450 mg, more preferably 800±300 mg, still more preferably 800±200 mg, yet more preferably 800±150 mg, most preferably 800±100 mg, and in particular 800±50 mg.

In a preferred embodiment, the pharmaceutical dosage form according to the invention is a round pharmaceutical dosage form, preferably having a diameter of e.g. 11 mm or 13 mm. Pharmaceutical dosage forms of this embodiment preferably have a diameter in the range of 1 mm to 30 mm, in particular in the range of 2 mm to 25 mm, more in particular 5 mm to 23 mm, even more in particular 7 mm to 13 mm; and a thickness in the range of 1.0 mm to 12 mm, in particular in the range of 2.0 mm to 10 mm, even more in particular from 3.0 mm to 9.0 mm, even further in particular from 4.0 mm to 8.0 mm.

In another preferred embodiment, the pharmaceutical dosage form according to the invention is an oblong pharmaceutical dosage form, preferably having a length of e.g. 17 mm and a width of e.g. 7 mm. In preferred embodiments, the pharmaceutical dosage form according to the invention has a length of e.g. 22 mm and a width of e.g. 7 mm; or a length of 23 mm and a width of 7 mm; whereas these embodiments are particularly preferred for capsules. Pharmaceutical dosage forms of this embodiment preferably have a lengthwise extension (longitudinal extension) of 1 mm to 30 mm, in particular in the range of 2 mm to 25 mm, more in particular 5 mm to 23 mm, even more in particular 7 mm to 20 mm; a width in the range of 1 mm to 30 mm, in particular in the range of 2 mm to 25 mm, more in particular 5 mm to 23 mm, even more in particular 7 mm to 13 mm; and a thickness in the range of 1.0 mm to 12 mm, in particular in the range of 2.0 mm to 10 mm, even more in particular from 3.0 mm to 9.0 mm, even further in particular from 4.0 mm to 8.0 mm.

The pharmaceutical dosage forms according to the invention can optionally be provided, partially or completely, with a conventional coating. The pharmaceutical dosage forms according to the invention are preferably film coated with conventional film coating compositions. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), poly(meth)acrylates, such as aminoalkylmethacrylate copolymers, methacrylic acid methylmethacrylate copolymers, methacrylic acid methylmethacrylate copolymers; vinyl polymers, such as polyvinylpyrrolidone, polyvinyl alcohol, polyvinylacetate; and natural film formers.

In a particularly preferred embodiment, the coating is water-soluble. In a preferred embodiment, the coating is based on polyvinyl alcohol, such as polyvinyl alcohol-partially hydrolyzed, and may additionally contain polyethylene glycol, such as macrogol 3350, and/or pigments. In another preferred embodiment, the coating is based on hydroxypropylmethylcellulose, preferably hypromellose type 2910 having a viscosity of 3 to 15 mPas.

The coating can be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5.

The coating can also be applied e.g. to improve the aesthetic impression and/or the taste of the pharmaceutical dosage forms and the ease with which they can be swallowed. Coating the pharmaceutical dosage forms according to the invention can also serve other purposes, e.g. improving stability and shelf-life. Suitable coating formulations comprise a film forming polymer such as, for example, polyvinyl alcohol or hydroxypropyl methylcellulose, e.g. hypromellose, a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Coated pharmaceutical dosage forms according to the invention are preferably prepared by first making the cores and subsequently coating said cores using conventional techniques, such as coating in a coating pan.

The subjects to which the pharmaceutical dosage forms according to the invention can be administered are not particularly limited. Preferably, the subjects are animals, more preferably human beings.

The pharmaceutical dosage form according to the invention contains a plurality of particles. The particles comprise a pharmacologically active compound, a polyalkylene oxide and a disintegrant. Preferably, the pharmacologically active compound is dispersed in the polyalkylene oxide and the disintegrant.

For the purpose of the specification, the term "particle" refers to a discrete mass of material that is solid, e.g. at 20° C. or at room temperature or ambient temperature. Preferably a particle is solid at 20° C. Preferably, the particles are monoliths. Preferably, the pharmacologically active compound and the polyalkylene oxide are intimately homogeneously distributed in the particles so that the particles do not contain any segments where either pharmacologically active compound is present in the absence of polyalkylene oxide or where polyalkylene oxide is present in the absence of pharmacologically active compound.

When the particles are film coated, the polyalkylene oxide is preferably homogeneously distributed in the core of the pharmaceutical dosage form, i.e. the film coating preferably does not contain polyalkylene oxide, but optionally polyalkylene glycol that differs from polyalkylene oxide in its lower molecular weight. Nonetheless, the film coating as such may of course contain one or more polymers, which however, preferably differ from the polyalkylene oxide contained in the core.

The particles are of macroscopic size, typically the average diameter is within the range of from 100 µm to 1500 µm, preferably 200 µm to 1500 µm, more preferably 300 µm to 1500 µm, still more preferably 400 µm to 1500 µm, most preferably 500 µm to 1500 µm, and in particular 600 µm to 1500 µm.

Preferably, the content of the particles in the pharmaceutical dosage forms according to the invention is at most 65 wt.-%, more preferably at most 60 wt.-%, still more preferably at most 55 wt.-%, yet more preferably at most 50 wt.-%, most preferably at most 45 wt.-% and in particular at most 40 wt.-%, based on the total weight of the pharmaceutical dosage form.

Preferably, the content of the particles in the pharmaceutical dosage forms according to the invention is at least 2.5 wt.-%, at least 3.0 wt.-%, at least 3.5 wt.-% or at least 4.0 wt.-%; more preferably at least 4.5 wt.-%, at least 5.0 wt.-%, at least 5.5 wt.-% or at least 6.0 wt.-%; most preferably at least 6.5 wt.-%, at least 7.0 wt.-%, at least 7.5 wt.-% or at least 8.0 wt.-%; and in particular at least 8.5 wt.-%, at least 9.0 wt.-%, at least 9.5 wt.-% or at least 10 wt.-%; based on the total weight of the pharmaceutical dosage form.

In a preferred embodiment, the content of the particles in the pharmaceutical dosage forms according to the invention is within the range of 10±7.5 wt.-%, more preferably 10±5.0 wt.-%, still more preferably 10±4.0 wt.-%, yet more preferably 10±3.0 wt.-%, most preferably 10±2.0 wt.-%, and in particular 10±1.0 wt.-%, based on the total weight of the pharmaceutical dosage form. In another preferred embodiment, the content of the particles in the pharmaceutical dosage forms according to the invention is within the range of 15±12.5 wt.-%, more preferably 15±10 wt.-%, still more preferably 15±8.0 wt.-%, yet more preferably 15±6.0 wt.-%, most preferably 15±4.0 wt.-%, and in particular 15±2.0 wt.-%, based on the total weight of the pharmaceutical dosage form. In still another preferred embodiment, the content of the particles in the pharmaceutical dosage forms according to the invention is within the range of 20±17.5 wt.-%, more preferably 20±15 wt.-%, still more preferably 20±12.5 wt.-%, yet more preferably 20±10 wt.-%, most preferably 20±7.5 wt.-%, and in particular 20±5 wt.-%, based on the total weight of the pharmaceutical dosage form. In yet another preferred embodiment, the content of the particles in the pharmaceutical dosage forms according to the invention is within the range of 25±17.5 wt.-%, more preferably 25±15 wt.-%, still more preferably 25±12.5 wt.-%, yet more preferably 25±10 wt.-%, most preferably 25±7.5 wt.-%, and in particular 25±5 wt.-%, based on the total weight of the pharmaceutical dosage form. In another preferred embodiment, the content of the particles in the pharmaceutical dosage forms according to the invention is within the range of 30±17.5 wt.-%, more preferably 30±15 wt.-%, still more preferably 30±12.5 wt.-%, yet more preferably 30±10 wt.-%, most preferably 30±7.5 wt.-%, and in particular 30±5 wt.-%, based on the total weight of the pharmaceutical dosage form. In still another preferred embodiment, the content of the particles in the pharmaceutical dosage forms according to the invention is within the range of 35±17.5 wt.-%, more preferably 35±15 wt.-%, still more preferably 35±12.5 wt.-%, yet more preferably 35±10 wt.-%, most preferably 35±7.5 wt.-%, and in particular 35±5 wt.-%, based on the total weight of the pharmaceutical dosage form.

The shape of the particles is not particularly limited. As the particles are preferably manufactured by hot-melt extrusion, preferred particles present in the pharmaceutical dosage forms according to the invention are generally cylindrical in shape. The diameter of such particles is therefore the diameter of their circular cross section. The cylindrical shape is caused by the extrusion process according to which the diameter of the circular cross section is a function of the extrusion die and the length of the cylinders is a function of the cutting length according to which the extruded strand of material is cut into pieces of preferably more or less predetermined length.

The suitability of cylindrical, i.e. a spherical particles for the manufacture of the pharmaceutical dosage forms according to the invention is unexpected. Typically, the aspect ratio is regarded as an important measure of the spherical shape. The aspect ratio is defined as the ratio of the maximal diameter ($d_{max}$) and its orthogonal Feret-diameter. For aspherical particles, the aspect ratio has values above 1. The smaller the value the more spherical is the particle. Aspect ratios below 1.1 are typically considered satisfactory, aspect ratios above 1.2, however, are typically considered not suitable for the manufacture of conventional pharmaceutical dosage forms. The inventors have surprisingly found that when manufacturing the pharmaceutical dosage forms according to the invention, even particles having aspect ratios above 1.2 can be processed without difficulties and that it is not necessary to provide spherical particles. In a preferred embodiment, the aspect ratio of the particles is at most 1.40, more preferably at most 1.35, still more preferably at most 1.30, yet more preferably at most 1.25, even more preferably at most 1.20, most preferably at most 1.15 and in particular at most 1.10. In another preferred embodiment, the aspect ratio of the particles is at least 1.10, more preferably at least 1.15, still more preferably at least 1.20, yet more preferably at least 1.25, even more preferably at least 1.30, most preferably at least 1.35 and in particular at least 1.40.

The particles in the pharmaceutical dosage forms according to the invention are of macroscopic size, i.e. typically have an average particle size of at least 50 µm, more preferably at least 100 µm, still more preferably at least 150 µm or at least 200 µm, yet more preferably at least 250 µm or at least 300 µm, most preferably at least 400 µm or at least 500 µm, and in particular at least 550 µm or at least 600 µm.

Preferred particles have an average length and average diameter of 1000 µm or less. When the particles are manufactured by extrusion technology, the "length" of particles is the dimension of the particles that is parallel to the direction of extrusion. The "diameter" of particles is the largest dimension that is perpendicular to the direction of extrusion.

Particularly preferred particles have an average diameter of less than 1000 µm, more preferably less than 800 µm, still more preferably of less than 650 µm. Especially preferred particles have an average diameter of less than 700 µm, particularly less than 600 µm, still more particularly less than 500 µm, e.g. less than 400 µm. Particularly preferred particles have an average diameter in the range 200 to 1000 µm, more preferably 400 to 800 µm, still more preferably 450 to 700 µm, yet more preferably 500 to 650 µm, e.g. 500 to 600 µm. Further preferred particles have an average diameter of between 300 µm and 400 µm, of between 400 µm and 500 µm, or of between 500 µm and 600 µm, or of between 600 µm and 700 µm or of between 700 µm and 800 µm.

Preferred particles that are present in the pharmaceutical dosage forms according to the invention have an average length of less than 1000 µm, preferably an average length of less than 800 µm, still more preferably an average length of less than 650 µm, e.g. a length of 800 µm, 700 µm 600 µm, 500 µm, 400 µm or 300 µm. Especially preferred particles have an average length of less than 700 µm, particularly less than 650 µm, still more particularly less than 550 µm, e.g. less than 450 µm. Particularly preferred particles therefore have an average length in the range 200-1000 µm, more preferably 400-800 µm, still more preferably 450-700 µm, yet more preferably 500-650 µm, e.g. 500-600 µm. The minimum average length of the microparticles is determined by the cutting step and may be, e.g. 500 µm, 400 µm, 300 µm or 200 µm.

In a preferred embodiment, the particles have (i) an average diameter of 1000±300 µm, more preferably 1000±250 µm, still more preferably 1000±200 µm, yet more preferably 1000±150 µm, most preferably 1000±100 µm, and in particular 1000±50 µm; and/or (ii) an average length of 1000±300 µm, more preferably 1000±250 µm, still more preferably 1000±200 µm, yet more preferably 1000±150 µm, most preferably 1000±100 µm, and in particular 1000±50 µm.

The size of particles may be determined by any conventional procedure known in the art, e.g. laser light scattering, sieve analysis, light microscopy or image analysis.

Preferably, the plurality of particles that is contained in the pharmaceutical dosage form according to the invention has an arithmetic average weight, in the following referred to as "aaw", wherein at least 70%, more preferably at least 75%, still more preferably at least 80%, yet more preferably at least 85%, most preferably at least 90% and in particular at least 95% of the individual particles contained in said plurality of particles has an individual weight within the range of aaw±30%, more preferably aaw±25%, still more preferably aaw±20%, yet more preferably aaw±15%, most preferably aaw±10%, and in particular aaw±5%. For example, if the pharmaceutical dosage form according to the invention contains a plurality of 100 particles and aaw of said plurality of particles is 1.00 mg, at least 75 individual particles (i.e. 75%) have an individual weight within the range of from 0.70 to 1.30 mg (1.00 mg±30%).

In a preferred embodiment, the particles are not film coated.

In another preferred embodiment, the particles are film coated. It has been surprisingly found that when the particles are film coated, the disintegration time and/or the drug release from the pharmaceutical dosage forms can be further accelerated, which is particularly significant for pharmaceutical dosage forms with immediate drug release.

The particles according to the invention can optionally be provided, partially or completely, with a conventional coating. The particles according to the invention are preferably film coated with conventional film coating compositions. Suitable coating materials are commercially available, e.g. under the trademarks Opadry® and Eudragit®.

When the particles are film coated, the content of the dried film coating is preferably at most 5 wt.-%, more preferably at most 4 wt.-%, still more preferably at most 3.5 wt.-%, yet more preferably at most 3 wt.-%, most preferably at most 2.5 wt.-%, and in particular at most 2 wt.-%, based on the total weight of the particles. In a particularly preferred embodiment, the weight increase based on the total weight of the pharmaceutical dosage form and/or based on the total weight of the particles (uncoated starting material) is within the range of from 3.0 to 4.7 wt.-%, more preferably 3.1 to 4.6 wt.-%, still more preferably 3.2 to 4.5 wt.-%, yet more preferably 3.3 to 4.4 wt.-%, most preferably 3.4 to 4.3 wt.-%, and in particular 3.5 to 4.2 wt.-%.

The tamper-resistant pharmaceutical dosage form according to the invention comprises a multitude of particles which comprise a pharmacologically active compound. The particles contain at least a pharmacologically active compound, a polyalkylene oxide and a disintegrant. Preferably, however, the particles contain additional pharmaceutical excipients such as antioxidants and plasticizers.

The pharmacologically active compound is dispersed in a matrix comprising the polyalkylene oxide and the disintegrant. In other words, the polyalkylene oxide and the disintegrant form a matrix in which the pharmacologically active compound is embedded.

The pharmacologically active compound is not particularly limited. Preferably, the pharmacologically active compound is an opioid.

In a preferred embodiment, the particles and the pharmaceutical dosage form, respectively, contain only a single pharmacologically active compound. In another preferred embodiment, the particles and the pharmaceutical dosage form, respectively, contain a combination of two or more pharmacologically active compounds.

Preferably, pharmacologically active compound is an active ingredient with potential for being abused. Active ingredients with potential for being abused are known to the person skilled in the art and comprise e.g. tranquilizers, stimulants, barbiturates, narcotics, opioids or opioid derivatives.

Preferably, the pharmacologically active compound exhibits psychotropic action.

Preferably, the pharmacologically active compound is selected from the group consisting of opiates, opioids, stimulants, tranquilizers, and other narcotics.

In a preferred embodiment, the pharmacologically active compound is an opioid. According to the ATC index, opioids are divided into natural opium alkaloids, phenylpiperidine derivatives, diphenylpropylamine derivatives, benzomorphan derivatives, oripavine derivatives, morphinan derivatives and others.

In another preferred embodiment, the pharmacologically active compound is a stimulant. Stimulants are psychoactive drugs that induce temporary improvements in either mental or physical functions or both. Examples of these kinds of effects may include enhanced wakefulness, locomotion, and alertness. Preferred stimulants are phenylethylamine derivatives. According to the ATC index, stimulants are contained in different classes and groups, e.g. psychoanaleptics, especially psychostimulants, agents used for ADHD and nootropics, particularly centrally acting sympathomimetics; and e.g. nasal preparations, especially nasal decongestants for systemic use, particularly sympathomimetics.

The following opiates, opioids, stimulants, tranquilizers or other narcotics are substances with a psychotropic action, i.e. have a potential of abuse, and hence are preferably contained in the pharmaceutical dosage form and the particles, respectively: alfentanil, allobarbital, allylprodine, alphaprodine, alprazolam, amfepramone, amphetamine, amphetaminil, amobarbital, anileridine, apocodeine, axomadol, barbital, bemidone, benzyl-morphine, bezitramide, bromazepam, brotizolam, buprenorphine, butobarbital, butorphanol, camazepam, carfentanil, cathine/D-norpseudoephedrine, cebranopadol, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dex-amphetamine, dextromoramide, dextropropoxyphene, dezocine, diampromide, diamorphone, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethyl-morphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, metha-done, methaqualone, 3-methylfentanyl, 4-methylfentanyl, methylphenidate, methylpheno-barbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone,

*Papaver somniferum*, papaveretum, pemoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, pseudoephedrine, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3 (3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethyl amino methyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethyl aminomethyl-cyclohex-1-enyl)-phenyl 2-(6-methoxy-naphthalen-2-yl) propionate, (RR-SS)-2-acetoxy-4-trifluoromethyl-benzoic acid 3-(2-dimethyl amino methyl-1-hydroxy-cyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethyl aminomethyl-1-hydroxy-cyclohexyl)-phenyl ester, (RR-SS)-2-hydroxy-4-methoxy-benzoic acid 3-(2-dimethyl amino methyl-1-hydroxy-cyclohexyl)-phenyl ester, (RR-SS)-2-hydroxy-5-nitro-benzoic acid 3-(2-dimethyl amino methyl-1-hydroxy-cyclohexyl)-phenyl ester, (RR-SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment, the pharmacologically active compound is selected from the group consisting of DPI-125, M6G (CE-04-410), ADL-5859, CR-665, NRP290 and sebacoyl dinalbuphine ester.

In a preferred embodiment, the pharmacologically active compound is an opioid selected from the group consisting of oxycodone, hydrocodone, oxymorphone, hydromorphone, morphine, tramadol, tapentadol, cebranopadol and the physiologically acceptable salts thereof.

In another preferred embodiment, the pharmacologically active compound is a stimulant selected from the group consisting of amphetamine, dex-amphetamine, dexmethylphenidate, atomoxetine, caffeine, ephedrine, phenylpropanolamine, phenylephrine, fencamphamin, fenozolone, fenetylline, methylenedioxymethamphetamine (MDMA), methylenedioxypyrovalerone (MDPV), prolintane, lisdexamfetamine, mephedrone, methamphetamine, methylphenidate, modafinil, nicotine, pemoline, phenylpropanolamine, propylhexedrine, dimethylamylamine, and pseudoephedrine.

In a particularly preferred embodiment, the pharmacologically active compound is methylphenidate.

In another particularly preferred embodiment, the pharmacologically active compound is lisdexamfetamine.

In another particularly preferred embodiment, the pharmacologically active compound is dexmethylphenidate.

The pharmacologically active compound may be present in form of a physiologically acceptable salt, e.g. physiologically acceptable acid addition salt.

Physiologically acceptable acid addition salts comprise the acid addition salt forms which can conveniently be obtained by treating the base form of the active ingredient with appropriate organic and inorganic acids. Active ingredients containing an acidic proton may be converted into their non-toxic metal or amine addition salt forms by treatment with appropriate organic and inorganic bases. The term addition salt also comprises the hydrates and solvent addition forms which the active ingredients are able to form. Examples of such forms are e.g. hydrates, alcoholates and the like.

In a preferred embodiment, the pharmacologically active compound is amphetamine aspartate monohydrate.

In another preferred embodiment, the pharmacologically active compound is dextroamphetamine saccharate.

In another preferred embodiment, the pharmacologically active compound is dextroamphetamine sulfate.

It has been surprisingly found that the content of the pharmacologically active compound in the pharmaceutical dosage form and in the particles, respectively, can be optimized in order to provide the best compromise between tamper-resistance, disintegration time and drug release, drug load, processability (especially tablettability) and patient compliance.

The pharmacologically active compound is present in the pharmaceutical dosage form in a therapeutically effective amount. The amount that constitutes a therapeutically effective amount varies according to the active ingredients being used, the condition being treated, the severity of said condition, the patient being treated, and the frequency of administration.

The content of the pharmacologically active compound in the pharmaceutical dosage form is not limited. The dose of the pharmacologically active compound which is adapted for administration preferably is in the range of 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the pharmacologically active compound that is contained in the pharmaceutical dosage form is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg.

Preferably, the content of the pharmacologically active compound is at least 0.5 wt.-%, based on the total weight of the pharmaceutical dosage form and/or based on the total weight of the particles.

Preferably, the content of the pharmacologically active compound is within the range of from 0.01 to 80 wt.-%, more preferably 0.1 to 50 wt.-%, still more preferably 1 to 25 wt.-%, based on the total weight of the pharmaceutical dosage form and/or based on the total weight of the particles.

In a preferred embodiment, the content of pharmacologically active compound is within the range of from 0.50±0.45 wt.-%, or 0.75±0.70 wt.-%, or 1.00±0.90 wt.-%, or 1.25±1.20 wt.-%, or 1.50±1.40 wt.-%, or 1.75±1.70 wt.-%, or 2.00±1.90 wt.-%, or 2.25±2.20 wt.-%, or 2.50±2.40 wt.-%; more preferably 0.50±0.40 wt.-%, or 0.75±0.60 wt.-%, or 1.00±0.80 wt.-%, or 1.25±1.10 wt.-%, or 1.50±1.25 wt.-%, or 1.75±1.50 wt.-%, or 2.00±1.75 wt.-%, or 2.25±2.00 wt.-%, or 2.50±2.25 wt.-%; still more preferably 0.50±0.35 wt.-%, or 0.75±0.50 wt.-%, or 1.00±0.70 wt.-%, or 1.25±1.00 wt.-%, or 1.50±1.15 wt.-%, or 1.75±1.30 wt.-%, or 2.00±1.50 wt.-%, or 2.25±1.90 wt.-%, or 2.50±2.10 wt.-%; yet more preferably 0.50±0.30 wt.-%, or 0.75±0.40 wt.-%, or 1.00±0.60 wt.-%, or 1.25±0.80 wt.-%, or 1.50±1.00 wt.-%, or 1.75±1.10 wt.-%, or 2.00±1.40 wt.-%, or 2.25±1.60 wt.-%, or 2.50±1.80 wt.-%; even more preferably 0.50±0.25 wt.-%, or 0.75±0.30 wt.-%, or 1.00±0.50 wt.-%, or 1.25±0.60 wt.-%, or 1.50±0.80 wt.-%, or 1.75±0.90 wt.-%, or 2.00±1.30 wt.-%, or 2.25±1.40 wt.-%, or 2.50±1.50 wt.-%; most preferably 0.50±0.20 wt.-%, or 0.75±0.25 wt.-%, or 1.00±0.40 wt.-%, or 1.25±0.50 wt.-%, or 1.50±0.60 wt.-%, or 1.75±0.70 wt.-%, or 2.00±1.10 wt.-%, or 2.25±1.20 wt.-%, or 2.50±1.30 wt.-%; and in particular 0.50±0.15 wt.-%, or 0.75±0.20 wt.-%, or 1.00±0.30 wt.-%, or 1.25±0.40 wt.-%, or 1.50±0.50 wt.-%, or 1.75±0.60 wt.-%, or 2.00±0.70 wt.-%, or 2.25±0.80 wt.-%, or 2.50±0.90 wt.-%; in each case based on the total weight of the pharmaceutical dosage form.

In a preferred embodiment, the content of pharmacologically active compound is within the range of from 2.0±1.9 wt.-%, or 2.5±2.4 wt.-%, or 3.0±2.9 wt.-%, or 3.5±3.4 wt.-%, or 4.0±3.9 wt.-%, or 4.5±4.4 wt.-%, or 5.0±4.9 wt.-%, or 5.5±5.4 wt.-%, or 6.0±5.9 wt.-%; more preferably 2.0±1.7 wt.-%, or 2.5±2.2 wt.-%, or 3.0±2.6 wt.-%, or 3.5±3.1 wt.-%, or 4.0±3.5 wt.-%, or 4.5±4.0 wt.-%, or 5.0±4.4 wt.-%, or 5.5±4.9 wt.-%, or 6.0±5.3 wt.-%; still more preferably 2.0±1.5 wt.-%, or 2.5±2.0 wt.-%, or 3.0±2.3 wt.-%, or 3.5±2.8 wt.-%, or 4.0±3.1 wt.-%, or 4.5±3.6 wt.-%, or 5.0±3.9 wt.-%, or 5.5±4.4 wt.-%, or 6.0±4.7 wt.-%; yet more preferably 2.0±1.3 wt.-%, or 2.5±1.8 wt.-%, or 3.0±2.0 wt.-%, or 3.5±2.5 wt.-%, or 4.0±2.7 wt.-%, or 4.5±3.2 wt.-%, or 5.0±3.4 wt.-%, or 5.5±3.9 wt.-%, or 6.0±4.1 wt.-%; even more preferably 2.0±1.1 wt.-%, or 2.5±1.6 wt.-%, or 3.0±1.7 wt.-%, or 3.5±2.2 wt.-%, or 4.0±2.4 wt.-%, or 4.5±2.8 wt.-%, or 5.0±2.9 wt.-%, or 5.5±3.4 wt.-%, or 6.0±3.5 wt.-%; most preferably 2.0±0.9 wt.-%, or 2.5±1.4 wt.-%, or 3.0±1.4 wt.-%, or 3.5±1.9 wt.-%, or 4.0±2.1 wt.-%, or 4.5±2.4 wt.-%, or 5.0±2.4 wt.-%, or 5.5±2.9 wt.-%, or 6.0±2.9 wt.-%; and in particular 2.0±0.7 wt.-%, or 2.5±1.2 wt.-%, or 3.0±1.1 wt.-%, or 3.5±1.6 wt.-%, or 4.0±1.8 wt.-%, or 4.5±2.0 wt.-%, or 5.0±1.9 wt.-%, or 5.5±2.4 wt.-%, or 6.0±2.3 wt.-%; in each case based on the total weight of the particles.

In a preferred embodiment, the content of pharmacologically active compound is within the range of from 10±6 wt.-%, more preferably 10±5 wt.-%, still more preferably 10±4 wt.-%, most preferably 10±3 wt.-%, and in particular 10±2 wt.-%, based on the total weight of the pharmaceutical dosage form and/or based on the total weight of the particles. In another preferred embodiment, the content of pharmacologically active compound is within the range of from 15±6 wt.-%, more preferably 15±5 wt.-%, still more preferably 15±4 wt.-%, most preferably 15±3 wt.-%, and in particular 15±2 wt.-%, based on the total weight of the pharmaceutical dosage form and/or based on the total weight of the particles. In a further preferred embodiment, the content of pharmacologically active compound is within the range of from 20±6 wt.-%, more preferably 20±5 wt.-%, still more preferably 20±4 wt.-%, most preferably 20±3 wt.-%, and in particular 20±2 wt.-%, based on the total weight of the pharmaceutical dosage form and/or based on the total weight of the particles. In another preferred embodiment, the content of pharmacologically active compound is within the range of from 25±6 wt.-%, more preferably 25±5 wt.-%, still more preferably 25±4 wt.-%, most preferably 25±3 wt.-%, and in particular 25±2 wt.-%, based on the total weight of the pharmaceutical dosage form and/or based on the total weight of the particles.

The skilled person may readily determine an appropriate amount of pharmacologically active compound to include in a pharmaceutical dosage form. For instance, in the case of analgesics, the total amount of pharmacologically active compound present in the pharmaceutical dosage form is that sufficient to provide analgesia. The total amount of pharmacologically active compound administered to a patient in a dose will vary depending on numerous factors including the nature of the pharmacologically active compound, the weight of the patient, the severity of the pain, the nature of other therapeutic agents being administered etc.

In a preferred embodiment, the pharmacologically active compound is contained in the pharmaceutical dosage form in an amount of 2.5±1 mg, 5.0±2.5 mg, 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, 160±5 mg, 170±5 mg, 180±5 mg, 190±5 mg, 200±5 mg, 210±5 mg, 220±5 mg, 230±5 mg, 240±5 mg, 250±5 mg, 260±5 mg, 270±5 mg, 280±5 mg, 290±5 mg, or 300±5 mg. In another preferred embodiment, the pharmacologically active compound is contained in the pharmaceutical dosage form in an amount of 2.5±1 mg, 5.0±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, 250±2.5 mg, 255±2.5 mg, 260±2.5 mg, or 265±2.5 mg.

In a particularly preferred embodiment, the pharmacologically active compound is tapentadol, preferably its HCl salt, and the pharmaceutical dosage form is adapted for administration once daily, twice daily, thrice daily or more frequently. In this embodiment, pharmacologically active compound is preferably contained in the pharmaceutical dosage form in an amount of from 25 to 100 mg.

In a particularly preferred embodiment, the pharmacologically active compound is oxymorphone, preferably its HCl salt, and the pharmaceutical dosage form is adapted for administration once daily, twice daily, thrice daily or more frequently. In this embodiment, the pharmacologically active compound is preferably contained in the pharmaceutical dosage form in an amount of from 5 to 40 mg. In another particularly preferred embodiment, the pharmacologically active compound is oxymorphone, preferably its HCl salt, and the pharmaceutical dosage form is adapted for administration once daily. In this embodiment, the pharmacologically active compound is preferably contained in the pharmaceutical dosage form in an amount of from 10 to 80 mg.

In another particularly preferred embodiment, the pharmacologically active compound is oxycodone, preferably its HCl salt, and the pharmaceutical dosage form is adapted for administration once daily, twice daily, thrice daily or more frequently. In this embodiment, the pharmacologically active compound is preferably contained in the pharmaceutical dosage form in an amount of from 5 to 80 mg.

In still another particularly preferred embodiment, the pharmacologically active compound is hydromorphone, preferably its HCl, and the pharmaceutical dosage form is adapted for administration once daily, twice daily, thrice daily or more frequently. In this embodiment, the pharmacologically active compound is preferably contained in the pharmaceutical dosage form in an amount of from 2 to 52 mg. In another particularly preferred embodiment, the pharmacologically active compound is hydromorphone, preferably its HCl, and the pharmaceutical dosage form is adapted for administration once daily, twice daily, thrice daily or more frequently. In this embodiment, the pharmacologically active compound is preferably contained in the pharmaceutical dosage form in an amount of from 4 to 104 mg.

In yet another particularly preferred embodiment, the pharmacologically active compound is hydrocodone, preferably its bitartrate salt, and the pharmaceutical dosage form is adapted for administration once daily, twice daily, thrice daily or more frequently. In this embodiment, the pharmacologically active compound is preferably contained in the pharmaceutical dosage form in an amount of from 2.5 to 10 mg.

The particles present in the pharmaceutical dosage forms according to the invention preferably comprise 3 to 75 wt.-% of pharmacologically active compound, more preferably 5 to 70 wt.-% of pharmacologically active compound, still more preferably 7.5 to 65 wt.-% of pharmacologically active compound, based on the total weight of the pharmaceutical dosage form and/or based on the total weight of the particles.

Preferably, the content of the pharmacologically active compound is at least 25 wt.-%, more preferably at least 30 wt.-%, still more preferably at least 35 wt.-%, yet more preferably at least 40 wt.-%, most preferably at least 45 wt.-%, based on the total weight of the pharmaceutical dosage form and/or based on the total weight of the particles.

Preferably, the content of the pharmacologically active compound is at most 70 wt.-%, more preferably at most 65 wt.-%, still more preferably at most 60 wt.-%, yet more preferably at most 55 wt.-%, most preferably at most 50 wt.-%, based on the total weight of the pharmaceutical dosage form and/or based on the total weight of the particles.

In a preferred embodiment, the content of the pharmacologically active compound is within the range of 35±30 wt.-%, more preferably 35±25 wt.-%, still more preferably 35±20 wt.-%, yet more preferably 35±15 wt.-%, most preferably 35±10 wt.-%, and in particular 35±5 wt.-%, based on the total weight of the pharmaceutical dosage form and/or based on the total weight of the particles. In another preferred embodiment, the content of the pharmacologically active compound is within the range of 45±30 wt.-%, more preferably 45±25 wt.-%, still more preferably 45±20 wt.-%, yet more preferably 45±15 wt.-%, most preferably 45±10 wt.-%, and in particular 45±5 wt.-%, based on the total weight of the pharmaceutical dosage form and/or based on the total weight of the particles. In still another preferred embodiment, the content of the pharmacologically active compound is within the range of 55±30 wt.-%, more preferably 55±25 wt.-%, still more preferably 55±20 wt.-%, yet more preferably 55±15 wt.-%, most preferably 55±10 wt.-%, and in particular 55±5 wt.-%, based on the total weight of the pharmaceutical dosage form and/or based on the total weight of the particles.

The pharmacologically active compound that is included in the preparation of the pharmaceutical dosage forms according to the invention preferably has an average particle size of less than 500 microns, still more preferably less than 300 microns, yet more preferably less than 200 or 100 microns. There is no lower limit on the average particle size and it may be, for example, 50 microns. The particle size of pharmacologically active compounds may be determined by any technique conventional in the art, e.g. laser light scattering, sieve analysis, light microscopy or image analysis. Generally speaking it is preferable that the largest dimension of the pharmacologically active compound particle be less than the size of the particles (e.g. less than the smallest dimension of the particles).

A skilled person knows how to determine pharmacokinetic parameters such as $t_{1/2}$, $T_{max}$, $C_{max}$, AUC and bioavailability. For the purposes of the description, the pharmacokinetic parameters, which may be determined from the blood plasma concentrations of 3-(2-dimethylaminomethylcyclohexyl)phenol, are defined as follows:

| | |
|---|---|
| $C_{max}$ | maximum measured plasma concentration of the active ingredient after single administration (=average peak plasma level) |
| $t_{max}$ | interval of time from administration of the active ingredient until $C_{max}$ is reached |
| AUC | total area of the plasma concentration/time curve including the subarea from the final measured value extrapolated to infinity |
| $t_{1/2}$ | half-life |

The above parameters are in each case stated as mean values of the individual values for all investigated patients/test subjects.

A person skilled in the art knows how the pharmacokinetic parameters of the active ingredient may be calculated from the measured concentrations of the active ingredient in the blood plasma. In this connection, reference may be made, for example, to Willi Cawello (ed.) *Parameters for Compartment-free Pharmacokinetics*, Shaker Verlag Aachen (1999).

In a preferred embodiment, the pharmacologically active compound is tapentadol or a physiologically acceptable salt thereof, e.g. the hydrochloride. Preferably, the pharmaceutical dosage form according to the invention provides a mean absolute bioavailability of tapentadol of at least 22%, more preferably at least 24%, still more preferably at least 26%, yet more preferably at least 28%, most preferably at least 30%, and in particular at least 32%. $T_{max}$ of tapentadol is preferably within the range of 1.25±1.20 h, more preferably 1.25±1.00 h, still more preferably 1.25±0.80 h, yet more preferably 1.25±0.60 h, most preferably 1.25±0.40 h, and in particular 1.25±0.20 h. $t_{1/2}$ of tapentadol is preferably within the range of 4.0±2.8 h, more preferably 4.0±2.4 h, still more preferably 4.0±2.0 h, yet more preferably 4.0±1.6 h, most preferably 4.0±1.2 h, and in particular 4.0±0.8 h. Preferably, when normalized to a dose of 100 mg tapentadol, $C_{max}$ of tapentadol is preferably within the range of 90±85 ng/mL, more preferably 90±75 ng/mL, still more preferably 90±65 ng/mL, yet more preferably 90±55 ng/mL, most preferably 90±45 ng/mL, and in particular 90±35 ng/mL; and/or AUC of tapentadol is preferably within the range of 420±400 ng/mL·h, more preferably 420±350 ng/mL·h, still more preferably 420±300 ng/mL·h, yet more preferably 420±250 ng/mL·h, most preferably 420±200 ng/mL·h, and in particular 420±150 ng/mL·h.

In another preferred embodiment, the pharmacologically active compound is oxycodone or a physiologically acceptable salt thereof, e.g. the hydrochloride. Preferably, the pharmaceutical dosage form according to the invention provides a mean absolute bioavailability of oxycodone of at least 40%, more preferably at least 45%, still more preferably at least 50%, yet more preferably at least 55%, most preferably at least 60%, and in particular at least 70%. $T_{max}$ of oxycodone is preferably within the range of 2.6±2.5 h, more preferably 2.6±2.0 h, still more preferably 2.6±1.8 h, yet more preferably 2.6±0.1.6 h, most preferably 2.6±1.4 h, and in particular 2.6±1.2 h. $t_{1/2}$ of oxycodone is preferably within the range of 3.8±3.5 h, more preferably 3.8±3.0 h, still more preferably 3.8±2.5 h, yet more preferably 3.8±2.0 h, most preferably 3.8±1.5 h, and in particular 3.8±1.0 h. Preferably, when normalized to a dose of 30 mg oxycodone, $C_{max}$ of oxycodone is preferably within the range of 40±35 ng/mL, more preferably 40±30 ng/mL, still more preferably 40±25 ng/mL, yet more preferably 40±20 ng/mL, most preferably 40±15 ng/mL, and in particular 40±10 ng/mL; and/or AUC of oxycodone is preferably within the range of 270±250 ng/mL·h, more preferably 270±200 ng/mL·h, still more preferably 270±150 ng/mL·h, yet more preferably 270±100 ng/mL·h, most preferably 270±75 ng/mL·h, and in particular 270±50 ng/mL·h.

In still another preferred embodiment, the pharmacologically active compound is hydrocodone or a physiologically acceptable salt thereof, e.g. the bitartrate. $T_{max}$ of hydrocodone is preferably within the range of 1.3±1.2 h, more preferably 1.3±1.0 h, still more preferably 1.3±0.8 h, yet more preferably 1.3±0.6 h, most preferably 1.3±0.4 h, and in particular 1.3±0.2 h. $t_{1/2}$ of hydrocodone is preferably within the range of 3.8±3.5 h, more preferably 3.8±3.0 h, still more preferably 3.8±2.5 h, yet more preferably 3.8±2.0 h, most preferably 3.8±1.5 h, and in particular 3.8±1.0 h.

In yet another preferred embodiment, the pharmacologically active compound is morphine or a physiologically acceptable salt thereof, e.g. the sulfate. Preferably, the pharmaceutical dosage form according to the invention provides a mean absolute bioavailability of morphine of at least 15%, more preferably at least 20%, still more preferably at least 25%, yet more preferably at least 30%, most preferably at least 35%, and in particular at least 40%. $T_{max}$ of morphine is preferably within the range of 0.625±0.60 h, more preferably 0.625±0.50 h, still more preferably 0.625±0.40 h, yet more preferably 0.625±0.30 h, most preferably 0.625±0.20 h, and in particular 0.625±0.15 h. Preferably, when normalized to a dose of 30 mg morphine sulfate, $C_{max}$ of morphine is preferably within the range of 25±20 ng/mL, more preferably 25±15 ng/mL, still more preferably 25±10 ng/mL, yet more preferably 25±5 ng/mL; and/or AUC of morphine is preferably within the range of 50±45 ng/mL·h, more preferably 50±40 ng/mL·h, still more preferably 50±35 ng/mL·h, yet more preferably 50±30 ng/mL·h, most preferably 50±25 ng/mL·h, and in particular 50±20 ng/mL·h.

In still another preferred embodiment, the pharmacologically active compound is amphetamine or a physiologically acceptable salt thereof. $T_{max}$ of amphetamine is preferably within the range of 1.7±1.2 h, more preferably 1.7±1.0 h, still more preferably 1.7±0.8 h, yet more preferably 1.7±0.6 h, most preferably 1.7±0.4 h, and in particular 1.7±0.2 h.

In still another preferred embodiment, the pharmacologically active compound is dex-amphetamine or a physiologically acceptable salt thereof, e.g. the sulfate. $T_{max}$ of dex-amphetamine is preferably within the range of 3.0±2.9 h, more preferably 3.0±2.5 h, still more preferably 3.0±2.1 h, yet more preferably 3.0±1.7 h, most preferably 3.0±1.3 h, and in particular 3.0±0.9 h. $t_{1/2}$ of dex-amphetamine is preferably within the range of 10±6.0 h, more preferably 10±5.0 h, still more preferably 10±4.0 h, yet more preferably 10±3.0 h, most preferably 10±2.0 h, and in particular 10±1.0 h.

The pharmaceutical dosage forms according to the invention may also comprise one or more additional pharmacologically active compounds. The additional pharmacologically active compound may be susceptible to abuse or another pharmaceutical. Additional pharmacologically active compounds may be present within the particles ("intragranular") or within the matrix ("extragranular"). Where an additional pharmacologically active compound is present intragranularly, it may be present either in combination with one or more pharmacologically active compounds within the same particles or in a discrete population of particles alone and separate from any other pharmacologically active compounds present in the pharmaceutical dosage form.

In a preferred embodiment, the pharmaceutical dosage form according to the invention, preferably the particles, comprise an opioid (agonist) as well as an opioid antagonist.

Any conventional opioid antagonist may be present, e.g. naltrexone or naloxone or their pharmaceutically acceptable salts. Naloxone, including its salts, is particularly preferred. The opioid antagonist may be present within the particles or within the matrix. Alternatively, opioid antagonist may be provided in separate particles to the pharmacologically active compounds. The preferred composition of such particles is the same as that described for pharmacologically active compound-containing particles.

The ratio of opioid agonist to opioid antagonist in the pharmaceutical dosage forms according to the invention is preferably 1:1 to 3:1 by weight, for example, 2:1 by weight.

In another preferred embodiment, neither the particles nor the pharmaceutical dosage form comprise any opioid antagonist.

The tamper-resistant pharmaceutical dosage form according to the invention comprises a multitude of particles which comprise a polyalkylene oxide, wherein the content of the polyalkylene oxide is at least 25 wt.-%, based on the total weight of the pharmaceutical dosage form and/or based on the total weight of the particles.

Preferably, the polyalkylene oxide is selected from polymethylene oxide, polyethylene oxide and polypropylene oxide, or copolymers thereof. Polyethylene oxide is preferred.

Preferably, the polyalkylene oxide has a weight average molecular weight of at least 500,000 g/mol. In a preferred embodiment, the polyalkylene oxide has a weight average molecular weight ($M_W$) or viscosity average molecular weight ($M_\eta$) of at least 750,000 g/mol, preferably at least 1,000,000 g/mol or at least 2,500,000 g/mol, more preferably in the range of 1,000,000 g/mol to 15,000,000 g/mol, and most preferably in the range of 5,000,000 g/mol to 10,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

Polyalkylene oxide may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of the specification, a polyalkylene glycol has a molecular weight of up to 20,000 g/mol whereas a polyalkylene oxide has a molecular weight of more than 20,000 g/mol. In a preferred embodiment, the weight average over all molecular weights of all polyalkylene oxides that are contained in the pharmaceutical dosage form is at least 200,000 g/mol. Thus, polyalkylene glycols, if any, are preferably not taken into consideration when determining the weight average molecular weight of polyalkylene oxide.

In a preferred embodiment, polyalkylene oxide is homogeneously distributed in the particles according to the invention. Preferably, the pharmacologically active compound and polyalkylene oxide are intimately homogeneously distributed in the particles so that the particles do not contain any segments where either pharmacologically active compound is present in the absence of polyalkylene oxide or where polyalkylene oxide is present in the absence of pharmacologically active compound.

When the particles are film coated, the polyalkylene oxide is preferably homogeneously distributed in the core of the particles, i.e. the film coating preferably does not contain polyalkylene oxide. Nonetheless, the film coating as such may of course contain one or more polymers, which however, preferably differ from the polyalkylene oxide contained in the core.

The polyalkylene oxide may be combined with one or more different polymers selected from the group consisting of polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(alk)acrylate, poly(hydroxy fatty acids), such as for example poly(3-hydroxybutyrate-co-3-hydroxyvalerate) (Biopol), poly(hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof (e.g., Poloxamer®), and mixtures of at least two of the stated polymers, or other polymers with the above characteristics.

Preferably, the molecular weight dispersity $M_w/M_n$ of polyalkylene oxide is within the range of 2.5±2.0, more preferably 2.5±1.5, still more preferably 2.5±1.0, yet more preferably 2.5±0.8, most preferably 2.5±0.6, and in particular 2.5±0.4.

The polyalkylene oxide preferably has a viscosity at 25° C. of 30 to 17,600 cP, more preferably 55 to 17,600 cP, still more preferably 600 to 17,600 cP and most preferably 4,500 to 17,600 cP, measured in a 5 wt.-% aqueous solution using a model RVF Brookfield viscosimeter (spindle no. 2/rotational speed 2 rpm); of 400 to 4,000 cP, more preferably 400 to 800 cP or 2,000 to 4,000 cP, measured on a 2 wt.-% aqueous solution using the stated viscosimeter (spindle no. 1 or 3/rotational speed 10 rpm); or of 1,650 to 10,000 cP, more preferably 1,650 to 5,500 cP, 5,500 to 7,500 cP or 7,500 to 10,000 cP, measured on a 1 wt.-% aqueous solution using the stated viscosimeter (spindle no. 2/rotational speed 2 rpm).

Polyethylene oxide that is suitable for use in the pharmaceutical dosage forms according to the invention is commercially available from Dow. For example, Polyox WSR N-12K, Polyox N-60K, Polyox WSR 301 NF or Polyox WSR 303NF may be used in the pharmaceutical dosage forms according to the invention. For details concerning the properties of these products, it can be referred to e.g. the product specification.

Preferably, the content of the polyalkylene oxide is within the range of from 25 to 80 wt.-%, more preferably 25 to 75 wt.-%, still more preferably 25 to 70 wt.-%, yet more preferably 25 to 65 wt.-%, most preferably 30 to 65 wt.-% and in particular 35 to 65 wt.-%, based on the total weight of the pharmaceutical dosage form and/or based on the total weight of the particles. In a preferred embodiment, the content of the polyalkylene oxide is at least 30 wt.-%, more preferably at least 35 wt.-%, still more preferably at least 40 wt.-%, yet more preferably at least 45 wt.-% and in particular at least 50 wt.-%, based on the total weight of the pharmaceutical dosage form and/or based on the total weight of the particles.

In a preferred embodiment, the overall content of polyalkylene oxide is within the range of 35±8 wt.-%, more preferably 35±6 wt.-%, most preferably 35±4 wt.-%, and in particular 35±2 wt.-%, based on the total weight of the pharmaceutical dosage form and/or based on the total weight of the particles. In another preferred embodiment, the overall content of polyalkylene oxide is within the range of 40±12 wt.-%, more preferably 40±10 wt.-%, most preferably 40±7 wt.-%, and in particular 40±3 wt.-%, based on the total weight of the pharmaceutical dosage form and/or based on the total weight of the particles. In still another preferred embodiment, the overall content of polyalkylene oxide is within the range of 45±16 wt.-%, more preferably 45±12 wt.-%, most preferably 45±8 wt.-%, and in particular 45±4 wt.-%, based on the total weight of the pharmaceutical dosage form and/or based on the total weight of the particles. In yet another preferred embodiment, the overall content of polyalkylene oxide is within the range of 50±20 wt.-%, more preferably 50±15 wt.-%, most preferably 50±10 wt.-%, and in particular 50±5 wt.-%, based on the total weight of the pharmaceutical dosage form and/or based on the total weight of the particles. In a further preferred embodiment, the overall content of polyalkylene oxide is within the range of 55±20 wt.-%, more preferably 55±15 wt.-%, most preferably 55±10 wt.-%, and in particular 55±5 wt.-%, based on the total weight of the pharmaceutical dosage form and/or based on the total weight of the particles. In still a further a preferred embodiment, the overall content of polyalkylene oxide is within the range of 60±20 wt.-%, more preferably 60±15 wt.-%, most preferably 60±10 wt.-%, and in particular 60±5 wt.-%. In a still further a preferred embodiment, the overall content of polyalkylene oxide is within the range of 65±20 wt.-%, more preferably 65±15 wt.-%, and most preferably 65±10 wt.-%, and in particular 65±5 wt.-%, based on the total weight of the pharmaceutical dosage form and/or based on the total weight of the particles.

Preferably, the relative weight ratio of the polyalkylene oxide to the pharmacologically active compound is within the range of 30:1 to 1:10, more preferably 20:1 to 1:1, still more preferably 15:1 to 5:1, yet more preferably 14:1 to 6:1, most preferably 13:1 to 7:1, and in particular 12:1 to 8:1.

The tamper-resistant pharmaceutical dosage form according to the invention comprises a multitude of particles which comprise a disintegrant, wherein the content of the disintegrant is more than 5.0 wt.-%, based on the total weight of the pharmaceutical dosage form and/or based on the total weight of the particles.

In a preferred embodiment, particularly when the pharmaceutical dosage form is a capsule, the pharmaceutical dosage form contains the entire amount of disintegrant within the particles, i.e. outside the particles there is preferably no disintegrant. Furthermore, the disintegrant is preferably homogeneously distributed in the particles. Preferably, when the particles are coated, the coating does not contain disintegrant.

In another preferred embodiment, particularly when the pharmaceutical dosage form is a tablet, the pharmaceutical dosage form contains the disintegrant within the particles as well as outside the particles. In a preferred embodiment, the nature of disintegrant within the particle is identical with the nature of disintegrant outside the particles. However, different disintegrants inside the particles and outside the particles are also possible in accordance with the invention. Furthermore, the disintegrant is preferably homogeneously distributed in the particles. Preferably, when the particles are coated, the coating does not contain disintegrant.

Suitable disintegrants are known to the skilled person and are preferably selected from the group consisting of polysaccharides, starches, starch derivatives, cellulose derivatives, polyvinylpyrrolidones, acrylates, gas releasing substances, and the mixtures of any of the foregoing.

Preferred starches include but are not limited to "standard starch" (e.g. native maize starch) and pregelatinized starch (e.g. starch 1500).

Preferred starch derivatives include but are not limited to sodium starch glycolate (carboxymethyl starch sodium, e.g. Vivastar).

Preferred cellulose derivatives include but are not limited to croscarmellose sodium (=crosslinked sodium carboxymethylcellulose; e.g. Vivasol®), carmellose calcium (calcium carboxymethylcellulose), carmellose sodium (sodium carboxymethylcellulose), low substituted carmellose sodium (low substituted sodium carboxymethylcellulose; average degree of substitution (DS) 0.20 to 0.40, Mr 80,000 to 600,000 g/mol, CAS 9004-32-4, E 466), low substituted hydroxypropylcellulose (having a content of propyl groups within the range of from 5 to 16%; CAS 9004-64-2).

Preferred acrylates include but are not limited to carbopol.

Preferred polyvinylpyrrolidones include but are not limited to crospovidone (PVP Preferred gas releasing substances include but are not limited to sodium bicarbonate.

Preferred disintegrants include but are not limited to crosslinked sodium carboxymethylcellulose (Na-CMC) (e.g. Crosscarmellose, Vivasol®, Ac-Di-Sol®); crosslinked casein (e.g. Esma-Spreng®); polysaccharide mixtures obtained from soybeans (e.g. Emcosoy®); maize starch or pretreated maize starch (e.g. Amijel5; alginic acid, sodium alginate, calcium alginate; polyvinylpyrrolidone (PVP) (e.g. Kollidone®, Polyplasdone®, Polydone®); crosslinked polyvinylpyrrolidone (PVP CI) (e.g. Polyplasdone® XL); starch and pretreated starch such as sodium carboxymethyl starch (=sodium starch glycolate, e.g. Explotab®, Prejel®, Primotab® ET, Starch® 1500, Ulmatryl®, and the mixtures thereof. Crosslinked polymers are particularly preferred disintegrants, especially crosslinked sodium carboxymethylcellulose (Na-CMC) or crosslinked polyvinylpyrrolidone (PVP CI).

Particularly preferred disintegrants are selected from the group consisting of
  crosslinked sodium carboxymethylcellulose (Na-CMC) (e.g. Crosscarmellose, Vivasol®, Ac-Di-Sol®);
  crosslinked casein (e.g. Esma-Spreng®);
  alginic acid, sodium alginate, calcium alginate;
  polysaccharide mixtures obtained from soybeans (e.g. Emcosoy®);
  starch and pretreated starch such as sodium carboxymethyl starch (=sodium starch glycolate, e.g. Explotab®, Prejel®, Primotab® ET, Starch® 1500, Ulmatryl®;
  maize starch or pretreated maize starch (e.g. Amijel®);
  and mixtures of any of the foregoing.

Preferably, the content of the disintegrant is at least 6.0 wt.-%, at least 7.0 wt.-%, at least 8.0 wt.-%, at least 9.0 wt.-%, or at least 10 wt.-%, more preferably at least 12 wt.-%, still more preferably at least 14 wt.-%, yet more preferably at least 15 wt.-%, even more preferably at least 16 wt.-%, most preferably at least 18 wt.-%, and in particular at least 19 wt.-%, based on the total weight of the pharmaceutical dosage form and/or based on the total weight of the particles.

It has been surprisingly found that the content of disintegrant typically has an optimum at which it provides the best balance of immediate release properties on the one hand and resistance against solvent extraction on the other hand. Said optimum may vary, but preferably is within the range of from about 10 wt.-% to about 20 wt.-%, relative to the total weight of the pharmaceutical dosage form and/or based on the total weight of the particles.

In a preferred embodiment, the content of the disintegrant in the pharmaceutical dosage form is within the range of 15±9.0 wt.-%, more preferably 15±8.5 wt.-%, still more preferably 15±8.0 wt.-%, yet more preferably 15±7.5 wt.-%, most preferably 15±7.0 wt.-%, and in particular 15±6.5 wt.-%, based on the total weight of the pharmaceutical dosage form and/or based on the total weight of the particles. In still another preferred embodiment, the content of the disintegrant in the pharmaceutical dosage form is within the range of 15±6.0 wt.-%, more preferably 15±5.5 wt.-%, still more preferably 15±5.0 wt.-%, yet more preferably 15±4.5 wt.-%, most preferably 15±4.0 wt.-%, and in particular 15±3.5 wt.-%, based on the total weight of the pharmaceutical dosage form and/or based on the total weight of the particles. In another preferred embodiment, the content of the disintegrant in the pharmaceutical dosage form is within the range of 15±3.0 wt.-%, more preferably 15±2.5 wt.-%, still more preferably 15±2.0 wt.-%, yet more preferably 15±1.5 wt.-%, most preferably 15±1.0 wt.-%, and in particular 15±0.5 wt.-%, based on the total weight of the pharmaceutical dosage form and/or based on the total weight of the particles.

In another preferred embodiment, the content of the disintegrant in the pharmaceutical dosage form is within the range of 20±15 wt.-% or 20±14 wt.-%, more preferably 20±13 wt.-%, still more preferably 20±12 wt.-%, yet more preferably 20±11 wt.-%, most preferably 20±10 wt.-%, and in particular 20±9.5 wt.-%, based on the total weight of the pharmaceutical dosage form and/or based on the total weight of the particles. In another preferred embodiment, the content of the disintegrant in the pharmaceutical dosage form is within the range of 20±9.0 wt.-%, more preferably 20±8.5 wt.-%, still more preferably 20±8.0 wt.-%, yet more preferably 20±7.5 wt.-%, most preferably 20±7.0 wt.-%, and in particular 20±6.5 wt.-%, based on the total weight of the pharmaceutical dosage form and/or based on the total weight of the particles. In still another preferred embodiment, the content of the disintegrant in the pharmaceutical dosage form is within the range of 20±6.0 wt.-%, more preferably 20±5.5 wt.-%, still more preferably 20±5.0 wt.-%, yet more preferably 20±4.5 wt.-%, most preferably 20±4.0 wt.-%, and in particular 20±3.5 wt.-%, based on the total weight of the pharmaceutical dosage form and/or based on the total weight of the particles. In another preferred embodiment, the content of the disintegrant in the pharmaceutical dosage form is within the range of 20±3.0 wt.-%, more preferably 20±2.5 wt.-%, still more preferably 20±2.0 wt.-%, yet more preferably 20±1.5 wt.-%, most preferably 20±1.0 wt.-%, and in particular 20±0.5 wt.-%, based on the total weight of the pharmaceutical dosage form and/or based on the total weight of the particles.

In still another preferred embodiment, the content of the disintegrant in the pharmaceutical dosage form is within the range of 25±9.0 wt.-%, more preferably 25±8.5 wt.-%, still more preferably 25±8.0 wt.-%, yet more preferably 25±7.5 wt.-%, most preferably 25±7.0 wt.-%, and in particular 25±6.5 wt.-%, based on the total weight of the pharmaceutical dosage form and/or based on the total weight of the particles. In still another preferred embodiment, the content of the disintegrant in the pharmaceutical dosage form is within the range of 25±6.0 wt.-%, more preferably 25±5.5 wt.-%, still more preferably 25±5.0 wt.-%, yet more preferably 25±4.5 wt.-%, most preferably 25±4.0 wt.-%, and in particular 25±3.5 wt.-%, based on the total weight of the pharmaceutical dosage form and/or based on the total weight of the particles. In another preferred embodiment, the content of the disintegrant in the pharmaceutical dosage form is within the range of 25±3.0 wt.-%, more preferably 25±2.5 wt.-%, still more preferably 25±2.0 wt.-%, yet more preferably 25±1.5 wt.-%, most preferably 25±1.0 wt.-%, and in particular 25±0.5 wt.-%, based on the total weight of the pharmaceutical dosage form and/or based on the total weight of the particles.

When the pharmaceutical dosage form according to the invention contains more than a single disintegrant, e.g. a mixture of two different disintegrants, the above percentages preferably refer to the total content of disintegrants.

Preferably, the relative weight ratio of the polyalkylene oxide to the disintegrant is within the range of 8:1 to 1:5, more preferably 7:1 to 1:4, still more preferably 6:1 to 1:3, yet more preferably 5:1 to 1:2, most preferably 4:1 to 1:1, and in particular 3:1 to 2:1.

Preferably, the relative weight ratio of the pharmacologically active ingredient to the disintegrant is within the range of 4:1 to 1:10, more preferably 3:1 to 1:9, still more preferably 2:1 to 1:8, yet more preferably 1:1 to 1:7, most preferably 1:2 to 1:6, and in particular 1:3 to 1:5.

The pharmaceutical dosage form may contain a single disintegrant or a mixture of different disintegrants. Preferably, the pharmaceutical dosage form contains a single disintegrant.

Preferably, the pharmaceutical dosage form and/or the particles according to the invention additionally comprise a gelling agent, which is preferably a polysaccharide.

While the gelling agent may principally contribute to the overall resistance against solvent extraction of the pharmaceutical dosage form according to the invention, it has been unexpectedly found that one or more disintegrants in comparatively high amounts in combination with one or more gelling agents are of particular advantage in this regard. It has been surprisingly found that the combination of one or more disintegrants in comparatively high amounts with one or more gelling agent is robust against variation of the pharmacologically active ingredient. Thus, according to the present invention exchanging a given pharmacologically active ingredient by another pharmacologically active ingredient does preferably not substantially alter the overall resistance against solvent extraction of the pharmaceutical dosage form according to the invention As used herein the term "gelling agent" is used to refer to a compound that, upon contact with a solvent (e.g. water), absorbs the solvent and swells, thereby forming a viscous or semi-viscous substance. Preferred gelling agents are not cross-linked. This substance may moderate pharmacologically active compound release from the particles in both aqueous and aqueous alcoholic media. Upon full hydration, a thick viscous solution or dispersion is typically produced that significantly reduces and/or minimizes the amount of free solvent which can contain an amount of solubilized pharmacologically active compound, and which can be drawn into a syringe. The gel that is formed may also reduce the overall amount of pharmacologically active compound extractable with the solvent by entrapping the pharmacologically active compound within a gel structure. Thus the gelling agent may play an important role in conferring tamper-resistance to the pharmaceutical dosage forms according to the invention.

Gelling agents include pharmaceutically acceptable polymers, typically hydrophilic polymers, such as hydrogels. Representative examples of gelling agents include gums like xanthan gum, carrageenan, locust bean gum, guar, tragacanth, acaica (gum arabic), karaya, tara and gellan gum; polyethylene oxide, polyvinyl alcohol, hydroxypropylmethyl cellulose, carbomers, poly(uronic) acids and mixtures thereof.

Preferably, the content of the gelling agent, preferably xanthan gum, is at least 1.0 wt.-%, more preferably at least 2.0 wt.-%, still more preferably at least 3.0 wt.-%, most preferably at least 4.0 wt.-%, based on the total weight of the pharmaceutical dosage form and/or based on the total weight of the particles.

Preferably, the content of the gelling agent, preferably xanthan gum, is within the range of 5.0±4.5 wt.-%, more preferably 5.0±4.0 wt.-%, still more preferably 5.0±3.5 wt.-%, yet more preferably 5.0±3.0 wt.-%, even more preferably 5.0±2.5 wt.-%, most preferably 5.0±2.0 wt.-%, and in particular 5.0±1.5 wt.-%, based on the total weight of the pharmaceutical dosage form and/or based on the total weight of the particles.

Preferably, the relative weight ratio of disintegrant:gelling agent is within the range of from 11:1 to 1:5, more preferably 10:1 to 1:4, still more preferably 9:1 to 1:3, yet more preferably 8:1 to 1:2, even more preferably 7:1 to 1:1, most preferably 6:1 to 2:1, and in particular 5:1 to 3:1.

The pharmaceutical dosage form and/or the particles according to the invention may contain additional pharmaceutical excipients conventionally contained in pharmaceutical dosage forms in conventional amounts, such as antioxidants, preservatives, lubricants, plasticizer, fillers, binders, and the like.

The skilled person will readily be able to determine appropriate further excipients as well as the quantities of each of these excipients. Specific examples of pharmaceutically acceptable carriers and excipients that may be used to formulate the pharmaceutical dosage forms according to the invention are described in the Handbook of Pharmaceutical Excipients, American Pharmaceutical Association (1986).

Preferably, the pharmaceutical dosage form and/or the particles according to the invention further comprise an antioxidant. Suitable antioxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably present in quantities of 0.01 wt.-% to 10 wt.-%, more preferably of 0.03 wt.-% to 5 wt.-%, most preferably of 0.05 wt.-% to 2.5 wt.-%, based on the total weight of the pharmaceutical dosage form and/or based on the total weight of the particles.

In a preferred embodiment, the pharmaceutical dosage form and/or the particles according to the invention further comprise an acid, preferably citric acid. The amount of acid is preferably in the range of 0.01 wt.-% to 20 wt.-%, more preferably in the range of 0.02 wt.-% to 10 wt.-%, and still more preferably in the range of 0.05 wt.-% to 5 wt.-%, and most preferably in the range of 0.1 wt.-% to 1.0 wt.-%, based on the total weight of the pharmaceutical dosage form and/or based on the total weight of the particles.

In a preferred embodiment, the pharmaceutical dosage form and/or the particles according to the invention further comprise another polymer which is preferably selected from cellulose esters and cellulose ethers, in particular hydroxypropyl methylcellulose (HPMC).

The amount of the further polymer, preferably hydroxypropyl methylcellulose, preferably ranges from 0.1 wt.-% to 30 wt.-%, more preferably in the range of 1.0 wt.-% to 20 wt.-%, most preferably in the range of 2.0 wt.-% to 15 wt.-%, and in particular in the range of 3.5 wt.-% to 10.5 wt.-%, based on the total weight of the pharmaceutical dosage form and/or based on the total weight of the particles.

In a preferred embodiment, the relative weight ratio of the polyalkylene oxide to the further polymer is within the range of 4.5±2:1, more preferably 4.5±1.5:1, still more preferably 4.5±1:1, yet more preferably 4.5±0.5:1, most preferably 4.5±0.2:1, and in particular 4.5±0.1:1. In another preferred embodiment, the relative weight ratio of the polyalkylene oxide to the further polymer is within the range of 8±7:1, more preferably 8±6:1, still more preferably 8±5:1, yet more preferably 8±4:1, most preferably 8±3:1, and in particular 8±2:1. In still another preferred embodiment, the relative weight ratio of the polyalkylene oxide to the further polymer is within the range of 11±8:1, more preferably 11±7:1, still more preferably 11±6:1, yet more preferably 11±5:1, most preferably 11±4:1, and in particular 11±3:1.

In another preferred embodiment, the pharmaceutical dosage form and/or the particles according to the invention do not contain any further polymer besides the polyalkylene oxide and optionally, polyethylene glycol.

In a preferred embodiment, the pharmaceutical dosage form contains at least one lubricant. Preferably, the lubricant is contained in the pharmaceutical dosage form outside the particles, i.e. the particles as such preferably do not contain lubricant. In another preferred embodiment, the pharmaceutical dosage form contains no lubricant. Especially preferred lubricants are selected from magnesium stearate and stearic acid;
glycerides of fatty acids, including monoglycerides, diglycerides, triglycerides, and mixtures thereof; preferably of $C_6$ to $C_{22}$ fatty acids; especially preferred are partial glycerides of the $C_{16}$ to $C_{22}$ fatty acids such as glycerol behenat, glycerol palmitostearate and glycerol monostearate;
polyoxyethylene glycerol fatty acid esters, such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerolli-noleate, macrogol-20-glycerolmonostearate, macrogol-6-glycerolcaprylocaprate, macrogolglycerololeate; macrogolglycerolstearate, macrogolglycerolhydroxystearate, and macrogolglycerolrizinoleate;
polyglycolyzed glycerides, such as the one known and commercially available under the trade name "Labrasol";
fatty alcohols that may be linear or branched, such as cetylalcohol, stearylalcohol, cetylstearyl alcohol, 2-octyldodecane-1-ol and 2-hexyldecane-1-ol;
polyethylene glycols having a molecular weight between 10.000 and 60.000 g/mol; and
natural semi-synthetic or synthetic waxes, preferably waxes with a softening point of at least 50° C., more preferably 60° C., and in particular carnauba wax and bees wax.

Preferably, the amount of the lubricant ranges from 0.01 wt.-% to 10 wt.-%, more preferably in the range of 0.05 wt.-% to 7.5 wt.-%, most preferably in the range of 0.1 wt.-% to 5 wt.-%, and in particular in the range of 0.1 wt.-% to 1 wt.-%, based on the total weight of the pharmaceutical dosage form and/or based on the total weight of the particles.

Preferably, the pharmaceutical dosage form and/or the particles according to the invention further comprise a plasticizer. The plasticizer improves the processability of the polyalkylene oxide. A preferred plasticizer is polyalkylene glycol, like polyethylene glycol, triacetin, fatty acids, fatty acid esters, waxes and/or microcrystalline waxes. Particularly preferred plasticizers are polyethylene glycols, such as PEG 6000 (Macrogol 6000).

Preferably, the content of the plasticizer is within the range of from 0.5 to 30 wt.-%, more preferably 1.0 to 25 wt.-%, still more preferably 2.5 wt.-% to 22.5 wt.-%, yet more preferably 5.0 wt.-% to 20 wt.-%, most preferably 6 to 20 wt.-% and in particular 7 wt.-% to 17.5 wt.-%, based on the total weight of the pharmaceutical dosage form and/or based on the total weight of the particles.

In a preferred embodiment, the plasticizer is a polyalkylene glycol having a content within the range of 7±6 wt.-%, more preferably 7±5 wt.-%, still more preferably 7±4 wt.-%, yet more preferably 7±3 wt.-%, most preferably 7±2 wt.-%, and in particular 7±1 wt.-%, based based on the total weight of the pharmaceutical dosage form and/or based on the total weight of the particles. In another preferred embodiment, the plasticizer is a polyalkylene glycol having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the pharmaceutical dosage form and/or based on the total weight of the particles.

In a preferred embodiment, the relative weight ratio of the polyalkylene oxide to the polyalkylene glycol is within the range of 5.4±2:1, more preferably 5.4±1.5:1, still more preferably 5.4±1:1, yet more preferably 5.4±0.5:1, most preferably 5.4±0.2:1, and in particular 5.4±0.1:1. This ratio satisfies the requirements of relative high polyalkylene oxide content and good extrudability.

Plasticizers can sometimes act as a lubricant, and lubricants can sometimes act as a plasticizer.

In preferred compositions of the particles that are preferably hot-melt extruded and that are contained in the pharmaceutical dosage form according to the invention, the pharmacologically active ingredient is an opioid and the polyalkylene oxide is a polyethylene oxide with a weight average molecular weight within the range of from 0.5 to 15 million g/mol. Particularly preferred embodiments $A^1$ to $A^8$ are summarized in the table here below:

| [wt.-%] | $A^1$ | $A^2$ | $A^3$ | $A^4$ | $A^5$ | $A^6$ | $A^7$ | $A^8$ |
|---|---|---|---|---|---|---|---|---|
| opioid | 5.5 ± 5.0 | 5.5 ± 4.5 | 5.5 ± 4.0 | 5.5 ± 3.5 | 5.5 ± 3.0 | 5.5 ± 2.5 | 5.5 ± 2.0 | 5.5 ± 1.5 |
| polyethylene oxide | 55 ± 40 | 55 ± 35 | 55 ± 30 | 55 ± 25 | 55 ± 20 | 55 ± 15 | 55 ± 10 | 55 ± 5 |
| disintegrant | 20 ± 15 | 20 ± 13 | 20 ± 11 | 20 ± 9 | 20 ± 7 | 20 ± 5 | 20 ± 4 | 20 ± 3 |
| optionally, acid | 0.8 ± 0.7 | 0.8 ± 0.7 | 0.8 ± 0.5 | 0.8 ± 0.5 | 0.8 ± 0.5 | 0.8 ± 0.3 | 0.8 ± 0.3 | 0.8 ± 0.3 |
| optionally, plasticizer | 14 ± 13 | 14 ± 12 | 14 ± 11 | 14 ± 10 | 14 ± 9 | 14 ± 8 | 14 ± 7 | 14 ± 6 |
| optionally, antioxidant | 0.2 ± 0.1 | 0.2 ± 0.1 | 0.2 ± 0.1 | 0.2 ± 0.1 | 0.2 ± 0.1 | 0.2 ± 0.1 | 0.2 ± 0.1 | 0.2 ± 0.1 |
| optionally, gelling agent | 5.0 ± 4.5 | 5.0 ± 4.0 | 5.0 ± 3.5 | 5.0 ± 3.0 | 5.0 ± 2.5 | 5.0 ± 2.0 | 5.0 ± 1.5 | 5.0 ± 1.0 |

(all percentages relative to the total weight of the particles).

In the above table, "optionally" in the context of the acid, the plasticizer, the antioxidant and the gelling agent means that these excipients may independently of one another be contained in the particles or not and provided that they are contained in the particles, their content in wt.-% is as specified.

The pharmaceutical dosage form according to the invention preferably contains no antagonists for the pharmacologically active compound, preferably no antagonists against psychotropic substances, in particular no antagonists against opioids. Antagonists suitable for a given pharmacologically active compound are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

Further, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, *eucalyptus* oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither antagonists for the pharmacologically active compound nor bitter substances.

In a preferred embodiment, the pharmaceutical dosage form according to the invention is a tablet, wherein the particles are contained in a matrix of a matrix material. In the following, this preferred embodiment is referred to as the "preferred tablet according to the invention".

The preferred tablet according to the invention comprises subunits having different morphology and properties, namely drug-containing particles and matrix material, wherein the particles form a discontinuous phase within the matrix material. The particles typically have mechanical properties that differ from the mechanical properties of the matrix material. Preferably, the particles have a higher mechanical strength than the matrix material. The particles within the preferred tablet according to the invention can be visualized by conventional means such as solid state nuclear magnetic resonance spectroscopy, raster electron microscopy, terahertz spectroscopy and the like.

In the preferred tablet according to the invention, the particles are incorporated in a matrix material. From a macroscopic perspective, the matrix material preferably forms a continuous phase in which the particles are embedded as discontinuous phase.

Preferably, the matrix material is a homogenous coherent mass, preferably a homogeneous mixture of solid constituents, in which the particles are embedded thereby spatially separating the particles from one another. While it is possible that the surfaces of particles are in contact or at least in very close proximity with one another, the plurality of particles preferably cannot be regarded as a single continuous coherent mass within the preferred tablet according to the invention.

In other words, the preferred tablet according to the invention comprises the particles as volume element(s) of a first type in which the pharmacologically active compound, the polyalkylene oxide and the disintegrant are contained, preferably homogeneously, and the matrix material as volume element of a second type differing from the material that forms the particles, preferably containing neither pharmacologically active compound nor polyalkylene oxide, but optionally polyethylene glycol which differs from polyethylene oxide in its molecular weight.

A purpose of the matrix material in the preferred tablet according to the invention is to ensure rapid disintegration and subsequent release of the pharmacologically active compound from the disintegrated preferred tablet according to the invention, i.e. from the particles. Thus, the matrix material preferably does not contain any excipient that might have a retardant effect on disintegration and drug release, respectively. Thus, the matrix material preferably does not contain any polymer that is typically employed as matrix material in prolonged release formulations.

The preferred tablet according to the invention preferably comprises the matrix material in an amount of more than one third of the total weight of the preferred tablet according to the invention. Thus, the polyalkylene oxide that is contained in the particles of the preferred tablet according to the invention is preferably not also contained in the matrix material.

Preferably, the pharmacologically active compound which is contained in the particles of the preferred tablet according to the invention is preferably not also contained in the matrix material. Thus, in a preferred embodiment, the total amount of pharmacologically active compound contained in the preferred tablet according to the invention is present in the particles which form a discontinuous phase within the matrix material; and the matrix material forming a continuous phase does not contain any pharmacologically active compound.

Preferably, the content of the matrix material is at least 35 wt.-%, at least 37.5 wt.-% or at least 40 wt.-%; more preferably at least 42.5 wt.-%, at least 45 wt.-%, at least 47.5 wt.-% or at least 50 wt.-%; still more preferably at least 52.5 wt.-%, at least 55 wt.-%, at least 57.5 wt.-% or at least 60 wt.-%; yet more preferably at least 62.5 wt.-%, at least 65 wt.-%, at least 67.5 wt.-% or at least 60 wt.-%; most preferably at least 72.5 wt.-%, at least 75 wt.-%, at least 77.5 wt.-% or at least 70 wt.-%; and in particular at least 82.5 wt.-%, at least 85 wt.-%, at least 87.5 wt.-% or at least 90 wt.-%; based on the total weight of the preferred tablet according to the invention.

Preferably, the content of the matrix material is at most 90 wt.-%, at most 87.5 wt.-%, at most 85 wt.-%, or at most 82.5 wt.-%; more preferably at most 80 wt.-%, at most 77.5 wt.-%, at most 75 wt.-% or at most 72.5 wt.-%; still more preferably at most 70 wt.-%, at most 67.5 wt.-%, at most 65 wt.-% or at most 62.5 wt.-%; yet more preferably at most 60 wt.-%, at most 57.5 wt.-%, at most 55 wt.-% or at most 52.5 wt.-%; most preferably at most 50 wt.-%, at most 47.5 wt.-%, at most 45 wt.-% or at most 42.5 wt.-%; and in particular at most 40 wt.-%, at most 37.5 wt.-%, or at most 35 wt.-%; based on the total weight of the preferred tablet according to the invention.

In a preferred embodiment, the content of the matrix material is within the range of 40±5 wt.-%, more preferably 40±2.5 wt.-%, based on the total weight of the preferred tablet according to the invention. In another preferred embodiment, the content of the matrix material is within the range of 45±10 wt.-%, more preferably 45±7.5 wt.-%, still more preferably 45±5 wt.-%, and most preferably 45±2.5 wt.-%, based on the total weight of the preferred tablet according to the invention. In still another preferred embodiment, the content of the matrix material is within the range of 50±10 wt.-%, more preferably 50±7.5 wt.-%, still more preferably 50±5 wt.-%, and most preferably 50±2.5 wt.-%, based on the total weight of the preferred tablet according to the invention. In yet another preferred embodiment, the content of the matrix material is within the range of 55±10 wt.-%, more preferably 55±7.5 wt.-%, still more preferably 55±5 wt.-%, and most preferably 55±2.5 wt.-%, based on the total weight of the preferred tablet according to the invention.

Preferably, the matrix material is a mixture, preferably a homogeneous mixture of at least two different constituents, more preferably of at least three different constituents. In a preferred embodiment, all constituents of the matrix material are homogeneously distributed in the continuous phase that is formed by the matrix material.

The pharmaceutical dosage form according to the invention is tamper-resistant.

As used herein, the term "tamper-resistant" refers to pharmaceutical dosage forms that are resistant to conversion into a form suitable for misuse or abuse, particular for nasal and/or intravenous administration, by conventional means such as grinding in a mortar or crushing by means of a hammer. In this regard, the pharmaceutical dosage forms as such may be crushable by conventional means. However, the particles contained in the pharmaceutical dosage forms according to the invention preferably exhibit mechanical properties such that they cannot be pulverized by conventional means any further. As the particles are of macroscopic size and contain the pharmacologically active compound, they cannot be administered nasally thereby rendering the pharmaceutical dosage forms tamper-resistant. Preferably, when trying to tamper the dosage form in order to prepare a formulation suitable for abuse by intravenous administration, the liquid part of the formulation that can be separated from the remainder by means of a syringe is as less as possible, preferably it contains not more than 20 wt.-%, more preferably not more than 15 wt.-%, still more preferably not more than 10 wt.-%, and most preferably not more than 5 wt.-% of the originally contained pharmacologically active compound. Preferably, this property is tested by (i) dispensing a pharmaceutical dosage form that is either intact or has been manually comminuted by means of two spoons in 5 ml of purified water, (ii) heating the liquid up to its boiling point, (iii) boiling the liquid in a covered vessel for 5 min without the addition of further purified water, (iv) drawing up the hot liquid into a syringe (needle 21 G equipped with a cigarette filter), (v) determining the amount of the pharmacologically active compound contained in the liquid within the syringe.

Further, when trying to disrupt the pharmaceutical dosage forms by means of a hammer or mortar, the particles tend to adhere to one another thereby forming aggregates and agglomerates, respectively, which are larger in size than the untreated particles.

Preferably, tamper-resistance is achieved based on the mechanical properties of the particles so that comminution is avoided or at least substantially impeded. According to the invention, the term comminution means the pulverization of the particles using conventional means usually available to an abuser, for example a pestle and mortar, a hammer, a mallet or other conventional means for pulverizing under the action of force. Thus, tamper-resistance preferably means that pulverization of the particles using conventional means is avoided or at least substantially impeded.

Preferably, the mechanical properties of the particles according to the invention, particularly their breaking strength and deformability, substantially rely on the presence and spatial distribution of polyalkylene oxide, although their mere presence does typically not suffice in order to achieve said properties. The advantageous mechanical properties of the particles according to the invention may not automatically be achieved by simply processing pharmacologically active compound, polyalkylene oxide, and optionally further excipients by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

In general, the particles exhibiting the desired properties may be obtained only if, during preparation of the particles,
 suitable components
 in suitable amounts
 are exposed to
 a sufficient pressure
 at a sufficient temperature
 for a sufficient period of time.

Thus, regardless of the apparatus used, the process protocols must be adapted in order to meet the required criteria.

Therefore, the breaking strength and deformability of the particles is separable from the composition.

The particles contained in the pharmaceutical dosage form according to the invention preferably have a breaking strength of at least 300 N, at least 400 N, or at least 500 N, preferably at least 600 N, more preferably at least 700 N, still more preferably at least 800 N, yet more preferably at least 1000 N, most preferably at least 1250 N and in particular at least 1500 N.

In order to verify whether a particle exhibits a particular breaking strength of e.g. 300 N or 500 N it is typically not necessary to subject said particle to forces much higher than 300 N and 500 N, respectively. Thus, the breaking strength test can usually be terminated once the force corresponding to the desired breaking strength has been slightly exceeded, e.g. at forces of e.g. 330 N and 550 N, respectively.

The "breaking strength" (resistance to crushing) of a pharmaceutical dosage form and of a particle is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Pharmaceutical dosage forms, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture the particle (=breaking force). Therefore, for the purpose of the specification a particle does preferably not exhibit the desired breaking strength when it breaks, i.e., is fractured into at least two independent parts that are separated from one another. In another preferred embodiment, however, the particle is regarded as being broken if the force decreases by 50% (threshold value) of the highest force measured during the measurement (see below).

The particles according to the invention are distinguished from conventional particles that can be contained in pharmaceutical dosage forms in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles. Avoidance of pulverization virtually rules out oral or parenteral, in particular intravenous or nasal abuse.

Conventional particles typically have a breaking strength well below 200 N.

The breaking strength of conventional round pharmaceutical dosage forms/particles may be estimated according to the following empirical formula: Breaking Strength [in N]=10×Diameter Of The Pharmaceutical dosage form/Particle [in mm]. Thus, according to said empirical formula, a round pharmaceutical dosage form/particle having a breaking strength of at least 300 N would require a diameter of at least 30 mm). Such a particle, however, could not be swallowed, let alone a pharmaceutical dosage form containing a plurality of such particles. The above empirical formula preferably does not apply to the particles according to the invention, which are not conventional but rather special.

Further, the actual mean chewing force is 220 N (cf., e.g., P. A. Proeschel et al., J Dent Res, 2002, 81(7), 464-468). This means that conventional particles having a breaking strength well below 200 N may be crushed upon spontaneous chewing, whereas the particles according to the invention may preferably not.

Still further, when applying a gravitational acceleration of 9.81 m/s$^2$, 300 N correspond to a gravitational force of more than 30 kg, i.e. the particles according to the invention can preferably withstand a weight of more than 30 kg without being pulverized.

Methods for measuring the breaking strength of a pharmaceutical dosage form are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Pharmaceutical dosage forms". The test is intended to determine, under defined conditions, the resistance to crushing of pharmaceutical dosage forms and particles, respectively, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the pharmaceutical dosage form and particle, respectively. The apparatus is calibrated using a system with a precision of 1 Newton. The pharmaceutical dosage form and particle, respectively, is placed between the jaws, taking into account, where applicable, the shape, the break-mark and the inscription; for each measurement the pharmaceutical dosage form and particle, respectively, is oriented in the same way with respect to the direction of application of the force (and the direction of extension in which the breaking strength is to be measured). The measurement is carried out on 10 pharmaceutical dosage forms and particles, respectively, taking care that all fragments have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a pharmaceutical dosage form and particle, respectively, to fail (i.e., break) in a specific plane. The pharmaceutical dosage forms and particles, respectively, are generally placed between two platens, one of which moves to apply sufficient force to the pharmaceutical dosage form and particle, respectively, to cause fracture. For conventional, round (circular cross-section) pharmaceutical dosage forms and particles, respectively, loading occurs across their diameter (sometimes referred to as diametral loading), and fracture occurs in the plane. The breaking force of pharmaceutical dosage forms and particles, respectively, is commonly called hardness in the pharmaceutical literature; however, the use of this term is misleading. In material science, the term hardness refers to the resistance of a surface to penetration or indentation by a small probe. The term crushing strength is also frequently used to describe the resistance of pharmaceutical dosage forms and particle, respectively, to the application of a compressive load. Although this term describes the true nature of the test more accurately than does hardness, it implies that pharmaceutical dosage forms and particles, respectively, are actually crushed during the test, which is often not the case.

Alternatively, the breaking strength (resistance to crushing) can be measured in accordance with WO 2008/107149, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. A skilled person knows how to properly adjust the test speed, e.g. to 10 mm/min, 20 mm/min, or 40 mm/min, for example. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturer's test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centring device.

When using the testControl software (testXpert V10.11), the following exemplified settings and parameters have revealed to be useful: LE-position: clamping length 150 mm. LE-speed: 500 mm/min, clamping length after pre-travel: 195 mm, pre-travel speed: 500 mm/min, no pre-force control—pre-force: pre-force 1N, pre-force speed 10 mm/min—sample data: no sample form, measuring length traverse distance 10 mm, no input required prior to testing—testing/end of test; test speed: position-controlled 10 mm/min, delay speed shift: 1, force shut down threshold 50% $F_{max}$, no force threshold for break-tests, no max level variation, upper force limit: 600N—expansion compensation: no correction of measuring length—actions after testing: LE to be set after test, no unload of sample—TRS: data memory: TRS distance interval until break 1 TRS time interval 0.1 s, TRS force interval 1N—machine; traverse distance controller: upper soft end 358 mm, lower soft end 192 mm—lower test space. Parallel arrangement of the upper plate and the ambos should be ensured—these parts must not touch during or after testing. After testing, a small gap (e.g. 0.1 or 0.2 mm) should still be present between the two brackets in intimated contact with the tested particle, representing the remaining thickness of the deformed particle.

In a preferred embodiment, the particle is regarded as being broken if it is fractured into at least two separate pieces of comparable morphology. Separated matter having a morphology different from that of the deformed particle, e.g. dust, is not considered as pieces qualifying for the definition of breaking.

The particles according to the invention preferably exhibit mechanical strength over a wide temperature range, in addition to the breaking strength (resistance to crushing) optionally also sufficient hardness, yield strength, fatigue strength, impact resistance, impact elasticity, tensile strength, compressive strength and/or modulus of elasticity, optionally also at low temperatures (e.g. below −24° C., below −40° C. or possibly even in liquid nitrogen), for it to be virtually impossible to pulverize by spontaneous chewing, grinding in a mortar, pounding, etc. Thus, preferably, the comparatively high breaking strength of the particle according to the invention is maintained even at low or very low temperatures, e.g., when the pharmaceutical dosage form is initially chilled to increase its brittleness, for example to temperatures below −25° C., below −40° C. or even in liquid nitrogen.

The particle according to the invention is characterized by a certain degree of breaking strength. This does not mean that the particle must also exhibit a certain degree of hardness. Hardness and breaking strength are different physical properties. Therefore, the tamper-resistance of the pharmaceutical dosage form does not necessarily depend on the hardness of the particles. For instance, due to its breaking strength, impact strength, elasticity modulus and tensile strength, respectively, the particles can preferably be deformed, e.g. plastically, when exerting an external force, for example using a hammer, but cannot be pulverized, i.e., crumbled into a high number of fragments. In other words, the particles according to the invention are characterized by a certain degree of breaking strength, but not necessarily also by a certain degree of form stability.

Therefore, in the meaning of the specification, a particle that is deformed when being exposed to a force in a particular direction of extension but that does not break (plastic deformation or plastic flow) is preferably to be regarded as having the desired breaking strength in said direction of extension.

Preferred particles present in the pharmaceutical dosage forms according to the invention are those having a suitable tensile strength as determined by a test method currently accepted in the art. Further preferred particles are those having a Youngs Modulus as determined by a test method of the art. Still further preferred particles are those having an acceptable elongation at break.

Irrespective of whether the particles according to the invention have an increased breaking strength or nor, the particles according to the invention preferably exhibit a certain degree of deformability. The particles contained in the pharmaceutical dosage form according to the invention preferably have a deformability such that they show an increase, preferably a substantially steady increase of the force at a corresponding decrease of the displacement in the force-displacement-diagram when being subjected to a breaking strength test as described above.

Figure 2:
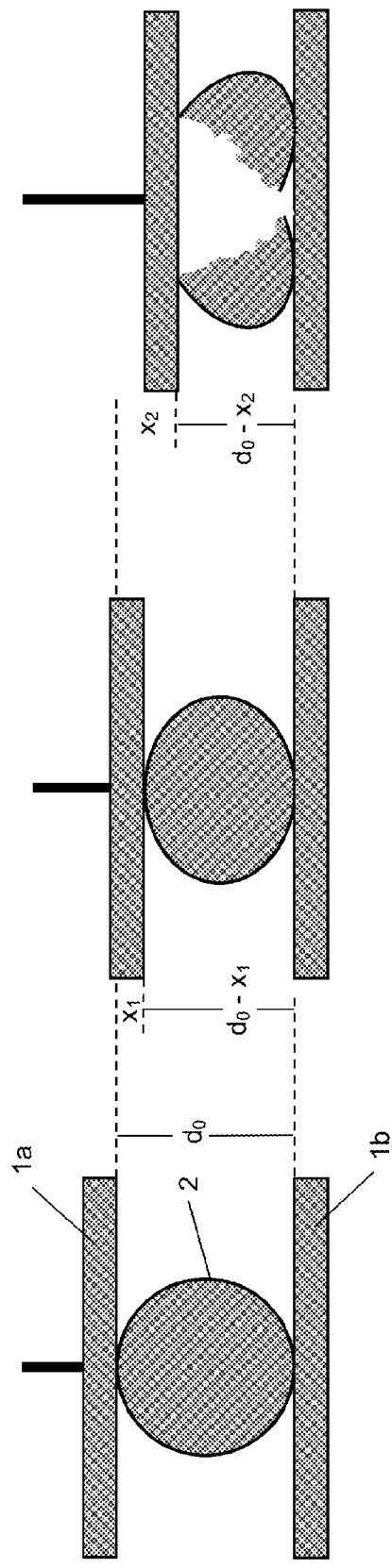
FIG. 2 illustrates the behavior of conventional particles when being subjected to a breaking strength test.
Figure 2:
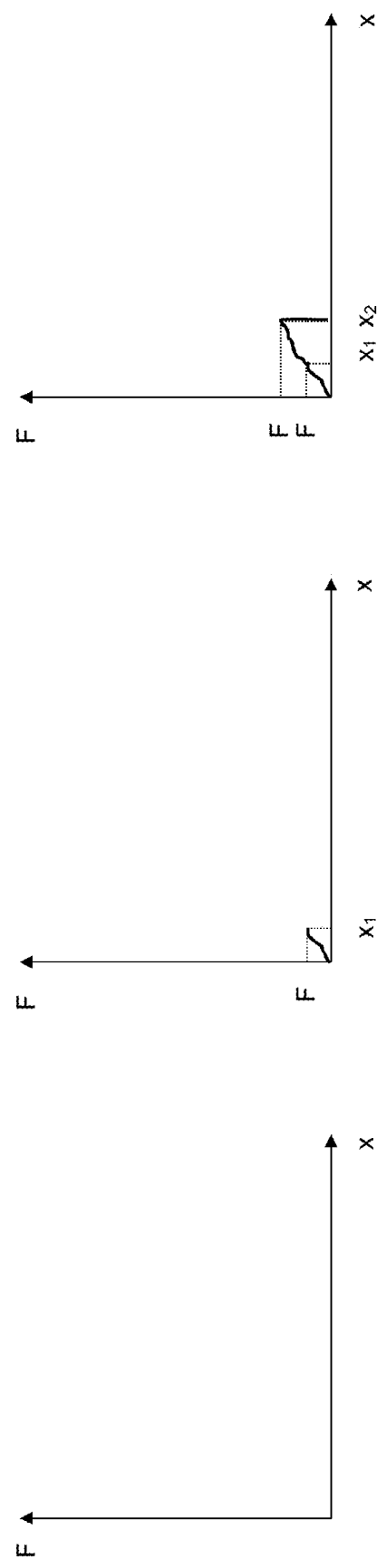
Figure 3:
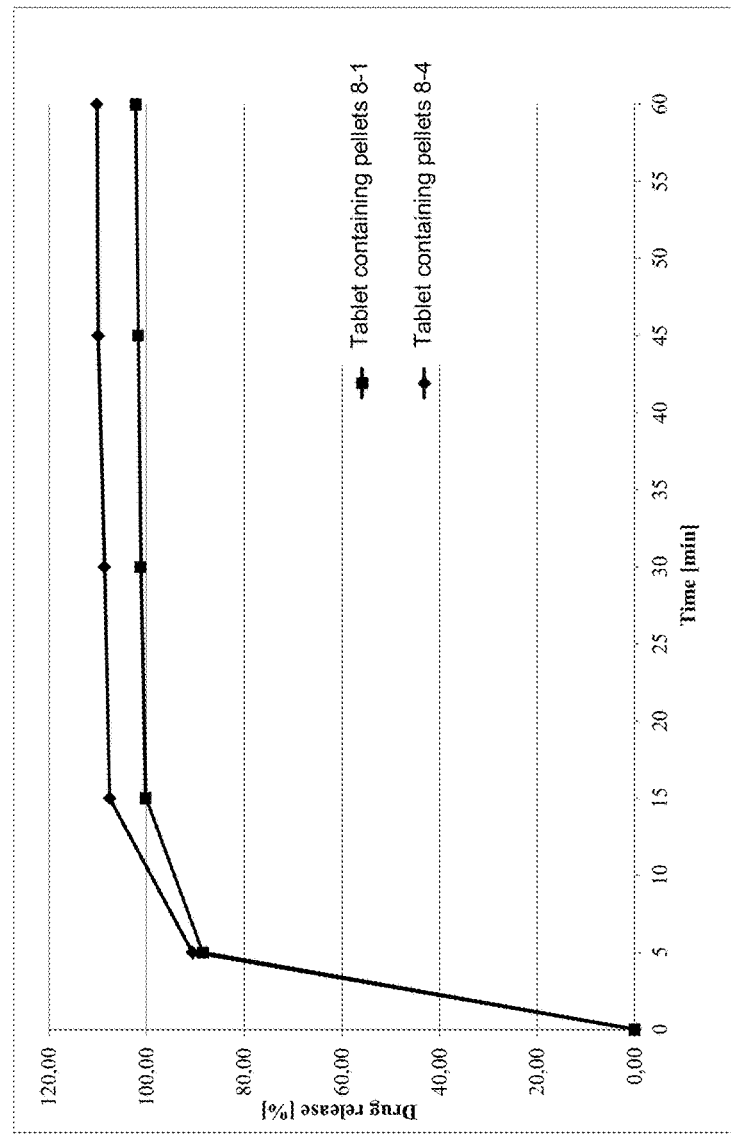
FIG. 3 provides in vitro dissolution data of tablets containing pellets.

This mechanical property, i.e. the deformability of the individual particles, is illustrated in FIGS. 1 and 2.

FIG. 1 schematically illustrates the measurement and the corresponding force-displacement-diagram. In particular, FIG. 1A shows the initial situation at the beginning of the measurement. The sample particle (2) is placed between upper jaw (1*a*) and lower jaw (1*b*) which each are in intimate contact with the surface of the particle (2). The initial displacement $d_0$ between upper jaw (1*a*) and lower jaw (1*b*) corresponds to the extension of the particle orthogonal to the surfaces of upper jaw (1*a*) and lower jaw (1*b*). At this time, no force is exerted at all and thus, no graph is displayed in the force-displacement-diagram below. When the measurement is commenced, the upper jaw is moved in direction of lower jaw (1*b*), preferably at a constant speed. FIG. 1B shows a situation where due to the movement of upper jaw (1*a*) towards lower jaw (1*b*) a force is exerted on particle (2). Because of its deformability, the particle (2) is flattened without being fractured. The force-displacement-diagram indicates that after a reduction of the displacement $d_0$ of upper jaw (1*a*) and lower jaw (1*b*) by distance $x_1$, i.e. at a displacement of $d_1=d_0-x_1$, a force $F_1$ is measured. FIG. 1C shows a situation where due to the continuous movement of upper jaw (1*a*) towards lower jaw (1*b*), the force that is exerted on particle (2) causes further deformation, although the particle (2) does not fracture. The force-displacement-diagram indicates that after a reduction of the displacement $d_0$ of upper jaw (1*a*) and lower jaw (1*b*) by distance $x_2$, i.e. at a displacement of $d_2=d_0-x_2$, a force $F_2$ is measured. Under these circumstances, the particle (2) has not been broken (fractured) and a substantially steady increase of the force in the force-displacement-diagram is measured.

In contrast, FIG. 2 schematically illustrates the measurement and the corresponding force-displacement-diagram of a conventional comparative particle not having the degree of deformability as the particles according to the invention. FIG. 2A shows the initial situation at the beginning of the measurement. The comparative sample particle (2) is placed between upper jaw (1a) and lower jaw (1b) which each are in intimate contact with the surface of the comparative particle (2). The initial displacement $d_0$ between upper jaw (1a) and lower jaw (1b) corresponds to the extension of the comparative particle orthogonal to the surfaces of upper jaw (1a) and lower jaw (1b). At this time, no force is exerted at all and thus, no graph is displayed in the force-displacement-diagram below. When the measurement is commenced, the upper jaw is moved in direction of lower jaw (1b), preferably at a constant speed. FIG. 2B shows a situation where due to the movement of upper jaw (1a) towards lower jaw (1b) a force is exerted on comparative particle (2). Because of some deformability, the comparative particle (2) is slightly flattened without being fractured. The force-displacement-diagram indicates that after a reduction of the displacement $d_0$ of upper jaw (1a) and lower jaw (1b) by distance $x_1$, i.e. at a displacement of $d_1=d_0-x_1$, a force $F_1$ is measured. FIG. 2C shows a situation where due to the continuous movement of upper jaw (1a) towards lower jaw (1b), the force that is exerted on particle (2) causes sudden fracture of the comparative particle (2). The force-displacement-diagram indicates that after a reduction of the displacement $d_0$ of upper jaw (1a) and lower jaw (1b) by distance $x_2$, i.e. at a displacement of $d_2=d_0-x_2$, a force $F_2$ is measured that suddenly drops when the particle fractures. Under these circumstances, the particle (2) has been broken (fractured) and no steady increase of the force in the force-displacement-diagram is measured. The sudden drop (decrease) of the force can easily be recognized and does not need to be quantified for the measurement. The steady increase in the force-displacement-diagram ends at displacement $d_2=d_0-x_2$ when the particle breaks.

In a preferred embodiment, the particles contained in the pharmaceutical dosage form according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), preferably at least until the displacement d of upper jaw (1a) and lower jaw (1b) has been reduced to a value of 90% of the original displacement $d_0$ (i.e. $d=0.9 \cdot d_0$), preferably to a displacement d of 80% of the original displacement $d_0$, more preferably to a displacement d of 70% of the original displacement $d_0$, still more preferably to a displacement d of 60% of the original displacement $d_0$, yet more preferably to a displacement d of 50% of the original displacement $d_0$, even more preferably to a displacement d of 40% of the original displacement $d_0$, most preferably to a displacement d of 30% of the original displacement $d_0$, and in particular to a displacement d of 20% of the original displacement $d_0$, or to a displacement d of 15% of the original displacement $d_0$, to a displacement d of 10% of the original displacement $d_0$, or to a displacement d of 5% of the original displacement $d_0$.

In another preferred embodiment, the particles contained in the pharmaceutical dosage form according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), preferably at least until the displacement d of upper jaw (1a) and lower jaw (1b) has been reduced to 0.80 mm or 0.75 mm, preferably 0.70 mm or 0.65 mm, more preferably 0.60 mm or 0.55 mm, still more preferably 0.50 mm or 0.45 mm, yet more preferably 0.40 mm or 0.35 mm, even more preferably 0.30 mm or 0.25 mm, most preferably 0.20 mm or 0.15 mm and in particular 0.10 or 0.05 mm.

In still another preferred embodiment, the particles contained in the pharmaceutical dosage form according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), at least until the displacement d of upper jaw (1a) and lower jaw (1b) has been reduced to 50% of the original displacement $d_0$ (i.e. $d=d_0/2$), whereas the force measured at said displacement ($d=d_0/2$) is at least 25 N or at least 50 N, preferably at least 75 N or at least 100 N, still more preferably at least 150 N or at least 200 N, yet more preferably at least 250 N or at least 300 N, even more preferably at least 350 N or at least 400 N, most preferably at least 450 N or at least 500 N, and in particular at least 625 N, or at least 750 N, or at least 875 N, or at least 1000 N, or at least 1250 N, or at least 1500 N.

In another preferred embodiment, the particles contained in the pharmaceutical dosage form according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), at least until the displacement d of upper jaw (1a) and lower jaw (1b) has been reduced by at least 0.1 mm, more preferably at least 0.2 mm, still more preferably at least 0.3 mm, yet more preferably at least 0.4 mm, even more preferably at least 0.5 mm, most preferably at least 0.6 mm, and in particular at least 0.7 mm, whereas the force measured at said displacement is within the range of from 5.0 N to 250 N, more preferably from 7.5 N to 225 N, still more preferably from 10 N to 200 N, yet more preferably from 15 N to 175 N, even more preferably from 20 N to 150 N, most preferably from 25 N to 125 N, and in particular from 30 N to 100 N.

In yet another embodiment, the particles contained in the pharmaceutical dosage form according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (1a) and lower jaw (1b) is reduced so that no further deformation takes place at said constant force, whereas at this equilibrated state the displacement d of upper jaw (1a) and lower jaw (1b) is at most 90% of the original displacement $d_0$ (i.e. $d \leq 0.9 \cdot d_0$), preferably at most 80% of the original displacement $d_0$ (i.e. $d \leq 0.8 \cdot d_0$), more preferably at most 70% of the original displacement $d_0$ (i.e. $d \leq 0.7 \cdot d_0$), still more preferably at most 60% of the original displacement $d_0$ (i.e. $d \leq 0.6 \cdot d_0$), yet more preferably at most 50% of the original displacement $d_0$ (i.e. $d \leq 0.5 \cdot d_0$), even more preferably at most 40% of the original displacement $d_0$ (i.e. $d \leq 0.4 \cdot d_0$), most preferably at most 30% of the original displacement $d_0$ (i.e. $d \leq 0.3 \cdot d_0$), and in particular at most 20% of the original displacement $d_0$ (i.e. $d \leq 0.2 \cdot d_0$), or at most 15% of the original displacement $d_0$ (i.e. $d \leq 0.15 \cdot d_0$), at most 10% of the original displacement $d_0$ (i.e. $d \leq 0.1 \cdot d_0$), or at most 5% of the original displacement $d_0$ (i.e. $d \leq 0.05 \cdot d_0$).

Preferably, the particles contained in the pharmaceutical dosage form according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (1a) and lower jaw (1b) is reduced so that no further deformation takes place at said constant force, whereas at this equilibrated state the displacement d of upper jaw (1a) and lower jaw (1b) is at most 0.80 mm or at most 0.75 mm, preferably at most 0.70 mm or at most 0.65 mm, more preferably at most 0.60 mm or at most 0.55 mm, still more preferably at most 0.50 mm or at most 0.45 mm, yet more preferably at most 0.40 mm or at most 0.35 mm, even more preferably at most 0.30 mm or at most 0.25 mm, most preferably at most 0.20 mm or at most 0.15 mm and in particular at most 0.10 or at most 0.05 mm.

In another embodiment, the particles contained in the pharmaceutical dosage form according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (1a) and lower jaw (1b) is reduced so that no further deformation takes place at said constant force, whereas at this equilibrated state the displacement d of upper jaw (1a) and lower jaw (1b) is at least 5% of the original displacement $d_0$ (i.e. $d \geq 0.05 \cdot d_0$), preferably at least 10% of the original displacement $d_0$ (i.e. $d \geq 0.1 \cdot d_0$), more preferably at least 15% of the original displacement $d_0$ (i.e. $d \geq 0.15 \cdot d_0$), still more preferably at least 20% of the original displacement $d_0$ (i.e. $d \geq 0.2 \cdot d_0$), yet more preferably at least 30% of the original displacement $d_0$ (i.e. $d \geq 0.3 \cdot d_0$), even more preferably at least 40% of the original displacement $d_0$ (i.e. $d \geq 0.4 \cdot d_0$), most preferably at least 50% of the original displacement $d_0$ (i.e. $d \geq 0.5 \cdot d_0$), and in particular at least 60% of the original displacement $d_0$ (i.e. $d \geq 0.6 \cdot d_0$), or at least 70% of the original displacement $d_0$ (i.e. $d \geq 0.7 \cdot d_0$), at least 80% of the original displacement $d_0$ (i.e. $d \geq 0.8 \cdot d_0$), or at least 90% of the original displacement $d_0$ (i.e. $d \geq 0.9 \cdot d_0$).

Preferably, the particles contained in the pharmaceutical dosage form according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (1a) and lower jaw (1b) is reduced so that no further deformation takes place at said constant force, whereas at this equilibrated state the displacement d of upper jaw (1a) and lower jaw (1b) is at least 0.05 mm or at least 0.10 mm, preferably at least 0.15 mm or at least 0.20 mm, more preferably at least 0.25 mm or at least 0.30 mm, still more preferably at least 0.35 mm or at least 0.40 mm, yet more preferably at least 0.45 mm or at least 0.50 mm, even more preferably at least 0.55 mm or at least 0.60 mm, most preferably at least 0.65 mm or at least 0.70 mm and in particular at least 0.75 or at least 0.80 mm.

The pharmaceutical dosage form according to the invention provides under in vitro conditions immediate release of the pharmacologically active compound in accordance with Ph. Eur. Preferably, the pharmaceutical dosage form according to the invention provides an release profile such that under in vitro conditions in 600 ml 0.1 M HCl (pH 1) at 75 rpm after 30 min (USP apparatus II) at least 90 wt.-% of the pharmacologically active ingredient that was originally contained in the dosage form have been released.

The term "immediate release" as applied to pharmaceutical dosage forms is understood by persons skilled in the art which has structural implications for the respective pharmaceutical dosage forms. The term is defined, for example, in the current issue of the US Pharmacopoeia (USP), General Chapter 1092, "THE DISSOLUTION PROCEDURE: DEVELOPMENT AND VALIDATION", heading "STUDY DESIGN", "Time Points". For immediate-release dosage forms, the duration of the procedure is typically 30 to 60 minutes; in most cases, a single time point specification is adequate for Pharmacopeia purposes. Industrial and regulatory concepts of product comparability and performance may require additional time points, which may also be required for product registration or approval. A sufficient number of time points should be selected to adequately characterize the ascending and plateau phases of the dissolution curve. According to the Biopharmaceutics Classification System referred to in several FDA Guidances, highly soluble, highly permeable drugs formulated with rapidly dissolving products need not be subjected to a profile comparison if they can be shown to release 85% or more of the active drug substance within 15 minutes. For these types of products a one-point test will suffice. However, most products do not fall into this category. Dissolution profiles of immediate-release products typically show a gradual increase reaching 85% to 100% at 30 to 45 minutes. Thus, dissolution time points in the range of 15, 20, 30, 45, and 60 minutes are usual for most immediate-release products.

Preferably, under physiological conditions the pharmaceutical dosage form according to the invention has released after 30 minutes at least 70%, more preferably at least 75%, still more preferably at least 80%, yet more preferably at least 82%, most preferably at least 84% and in particular at least 86% of the pharmacologically active compound originally contained in the pharmaceutical dosage form.

Preferably, under physiological conditions the pharmaceutical dosage form according to the invention has released after 10 minutes at least 70%, more preferably at least 73%, still more preferably at least 76%, yet more preferably at least 78%, most preferably at least 80% and in particular at least 82% of the pharmacologically active compound originally contained in the pharmaceutical dosage form.

Further preferred release profiles $B^1$ to $B^{10}$ are summarized in the table here below [all data in wt.-% of released pharmacologically active compound]:

| time | $B^1$ | $B^2$ | $B^3$ | $B^4$ | $B^5$ | $B^6$ | $B^7$ | $B^8$ | $B^9$ | $B^{10}$ |
|---|---|---|---|---|---|---|---|---|---|---|
| 10 min | ≥30 | ≥35 | ≥40 | ≥45 | ≥50 | ≥60 | ≥70 | ≥80 | ≥80 | ≥80 |
| 20 min | ≥50 | ≥55 | ≥60 | ≥65 | ≥70 | ≥75 | ≥80 | ≥85 | ≥90 | ≥95 |
| 30 min | ≥55 | ≥60 | ≥65 | ≥70 | ≥75 | ≥85 | ≥90 | ≥95 | ≥95 | ≥95 |
| 40 min | ≥60 | ≥65 | ≥70 | ≥80 | ≥85 | ≥90 | ≥95 | ≥95 | ≥95 | ≥95 |
| 50 min | ≥65 | ≥70 | ≥80 | ≥85 | ≥88 | ≥92 | ≥95 | ≥95 | ≥95 | ≥95 |
| 60 min | ≥75 | ≥80 | ≥85 | ≥90 | ≥92 | ≥94 | ≥95 | ≥95 | ≥95 | ≥95 |

Preferably, the release profile, the drug and the pharmaceutical excipients of the pharmaceutical dosage form according to the invention are stable upon storage, preferably upon storage at elevated temperature, e.g. 40° C., for 3 months in sealed containers.

In connection with the release profile "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

In connection with the drug and the pharmaceutical excipients "stable" means that the pharmaceutical dosage forms satisfy the requirements of EMEA concerning shelf-life of pharmaceutical products.

Suitable in vitro conditions are known to the skilled artisan. In this regard it can be referred to, e.g., the Eur. Ph. Preferably, the release profile is measured under the following conditions: Paddle apparatus equipped without sinker, 50 rpm, 37±5° C., 900 mL simulated intestinal fluid pH 6.8 (phosphate buffer) or pH 4.5. In a preferred embodiment, the rotational speed of the paddle is increased to 75 rpm.

In a preferred embodiment, the pharmaceutical dosage form according to the invention is adapted for administration once daily. In another preferred embodiment, the pharmaceutical dosage form according to the invention is adapted for administration twice daily. In still another preferred embodiment, the pharmaceutical dosage form according to the invention is adapted for administration thrice daily. In yet another preferred embodiment, the pharmaceutical dosage form according to the invention is adapted for administration more frequently than thrice daily, for example 4 times daily, 5 times daily, 6 times daily, 7 times daily or 8 times daily.

For the purpose of the specification, "twice daily" means equal or nearly equal time intervals, i.e., every 12 hours, or different time intervals, e.g., 8 and 16 hours or 10 and 14 hours, between the individual administrations.

For the purpose of the specification, "thrice daily" means equal or nearly equal time intervals, i.e., every 8 hours, or different time intervals, e.g., 6, 6 and 12 hours; or 7, 7 and 10 hours, between the individual administrations.

Preferably, the pharmaceutical dosage form according to the invention has under in vitro conditions a disintegration time measured in accordance with Ph. Eur. of at most 5 minutes, more preferably at most 4 minutes, still more preferably at most 3 minutes, yet more preferably at most 2.5 minutes, most preferably at most 2 minutes and in particular at most 1.5 minutes.

It has been surprisingly found that oral dosage forms can be designed that provide the best compromise between tamper-resistance, disintegration time and drug release, drug load, processability (especially tablettability) and patient compliance.

Tamper-resistance and drug release antagonize each other. While smaller particles should typically show a faster release of the pharmacologically active compound, tamper-resistance requires some minimal size of the particles in order to effectively prevent abuse, e.g. i.v. administration. The larger the particles are the less they are suitable for being abused nasally. The smaller the particles are the faster gel formation occurs. Thus, drug release on the one hand and tamper-resistance on the other hand can be optimized by finding the best compromise.

In a preferred embodiment of the pharmaceutical dosage form according to the invention, the particles are hot melt-extruded. Thus, the particles according to the invention are preferably prepared by melt-extrusion, although also other methods of thermoforming may be used in order to manufacture the particles according to the invention such as press-molding at elevated temperature or heating of particles that were manufactured by conventional compression in a first step and then heated above the softening temperature of the polyalkylene oxide in the particles in a second step to form hard pharmaceutical dosage forms. In this regards, thermoforming means the forming, or molding of a mass after the application of heat. In a preferred embodiment, the particles are thermoformed by hot-melt extrusion.

In a preferred embodiment, the particles are prepared by hot melt-extrusion, preferably by means of a twin-screw-extruder. Melt extrusion preferably provides a melt-extruded strand that is preferably cut into monoliths, which are then optionally compressed and formed into particles. Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C. The strands obtained by way of extrusion can either be subjected to the compression step as such or can be cut prior to the compression step. This cutting can be performed by usual techniques, for example using rotating knives or compressed air, at elevated temperature, e.g. when the extruded stand is still warm due to hot-melt extrusion, or at ambient temperature, i.e. after the extruded strand has been allowed to cool down. When the extruded strand is still warm, singulation of the extruded strand into extruded particles is preferably performed by cutting the extruded strand immediately after it has exited the extrusion die. It is possible to subject the extruded strands to the compression step or to the cutting step when still warm, that is more or less immediately after the extrusion step. The extrusion is preferably carried out by means of a twin-screw extruder.

The particles of the pharmaceutical dosage form according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

In general, the process for the production of the particles according to the invention preferably comprises the following steps:

(a) mixing all ingredients;
(b) optionally pre-forming the mixture obtained from step (a), preferably by applying heat and/or force to the mixture obtained from step (a), the quantity of heat supplied preferably not being sufficient to heat the polyalkylene oxide up to its softening point;
(c) hardening the mixture by applying heat and force, it being possible to supply the heat during and/or before the application of force and the quantity of heat supplied being sufficient to heat the polyalkylene oxide at least up to its softening point; and thereafter allowing the material to cool and removing the force
(d) optionally singulating the hardened mixture; and
(e) optionally providing a film coating.

Heat may be supplied directly, e.g. by contact or by means of hot gas such as hot air, or with the assistance of ultrasound; or is indirectly supplied by friction and/or shear. Force may be applied and/or the particles may be shaped for example by direct tabletting or with the assistance of a suitable extruder, particularly by means of a screw extruder equipped with one or two screws (single-screw-extruder and twin-screw-extruder, respectively) or by means of a planetary gear extruder.

The final shape of the particles may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the polyalkylene oxide. However, extrusion at lower temperatures, e.g. ambient temperature, is also possible and may be preferred.

In a preferred embodiment, the mixture of ingredients is heated and subsequently compressed under conditions (time, temperature and pressure) sufficient in order to achieve the desired mechanical properties, e.g. in terms of breaking strength and the like. This technique may be achieved e.g. by means of a tabletting tool which is either heated and/or which is filled with the heated mixture that is subsequently compressed without further supply of heat or with simultaneous additional supply of heat.

In another preferred embodiment, the mixture of ingredients is heated and simultaneously compressed under conditions (time, temperature and pressure) sufficient in order to achieve the desired mechanical properties, e.g. in terms of breaking strength and the like. This technique may be achieved e.g. by means of an extruder with one or more heating zones, wherein the mixture is heated and simultaneously subjected to extrusion forces finally resulting in a compression of the heated mixture.

In still another embodiment, the mixture of ingredients is compressed under ambient conditions at sufficient pressure and subsequently heated (cured) under conditions (time, temperature) sufficient in order to achieve the desired mechanical properties, e.g. in terms of breaking strength and the like. This technique may be achieved e.g. by means of a curing oven in which the compressed articles are cured for a sufficient time at a sufficient temperature, preferably without exerting any further pressure. Such process is further described e.g. in US 2009/0081290.

A particularly preferred process for the manufacture of the particles according to the invention involves hot-melt extrusion. In this process, the particles according to the invention are produced by thermoforming with the assistance of an extruder, preferably without there being any observable consequent discoloration of the extrudate.

This process is characterized in that
a) all components are mixed,
b) the resultant mixture is heated in the extruder at least up to the softening point of the polyalkylene oxide and extruded through the outlet orifice of the extruder by application of force,
c) the still plastic extrudate is singulated and formed into the particles or
d) the cooled and optionally reheated singulated extrudate is formed into the particles.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The, preferably molten, mixture which has been heated in the extruder at least up to the softening point of polyalkylene oxide is extruded from the extruder through a die with at least one bore, preferably a multitude of bores.

The process according to the invention requires the use of suitable extruders, preferably screw extruders. Screw extruders which are equipped with two screws (twin-screw-extruders) are particularly preferred.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of the polyalkylene oxide proceeding in the first zone, which is downstream from a feed zone and optionally mixing zone. The throughput of the mixture is preferably from 1.0 kg to 15 kg/hour. In a preferred embodiment, the throughput is from 0.5 kg/hour to 3.5 kg/hour. In another preferred embodiment, the throughput is from 4 to 15 kg/hour.

In a preferred embodiment, the die head pressure is within the range of from 25 to 200 bar. The die head pressure can be adjusted inter alia by die geometry, temperature profile, extrusion speed, number of bores in the dies, screw configuration, first feeding steps in the extruder, and the like.

The die geometry or the geometry of the bores is freely selectable. The die or the bores may accordingly exhibit a round, oblong or oval cross-section, wherein the round cross-section preferably has a diameter of 0.1 mm to 2 mm, preferably of 0.5 mm to 0.9 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the polyalkylene oxide and does not rise above a temperature at which the pharmacologically active compound to be processed may be damaged. Preferably, the temperature of the mixture to be extruded is adjusted to below 180° C., preferably below 150° C., but at least to the softening temperature of polyalkylene oxide. Typical extrusion temperatures are 120° C. and 150° C.

In a preferred embodiment, the extruder torque is within the range of from 30 to 95%. Extruder torque can be adjusted inter alia by die geometry, temperature profile, extrusion speed, number of bores in the dies, screw configuration, first feeding steps in the extruder, and the like.

After extrusion of the molten mixture and optional cooling of the extruded strand or extruded strands, the extrudates are preferably singulated. This singulation may preferably be performed by cutting up the extrudates by means of revolving or rotating knives, wires, blades or with the assistance of laser cutters.

Preferably, intermediate or final storage of the optionally singulated extrudate or the final shape of the particles according to the invention is performed under oxygen-free atmosphere which may be achieved, e.g., by means of oxygen-scavengers.

The singulated extrudate may be press-formed into particles in order to impart the final shape to the particles.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with desired mechanical properties, may be established by simple preliminary testing.

For example but not limiting, extrusion may be performed by means of a twin-screw-extruder type ZSE 18 or ZSE27 (Leistritz, Nürnberg, Germany), screw diameters of 18 or 27 mm. Screws having eccentric or blunt ends may be used. A heatable die with a round bore or with a multitude of bores each having a diameter of 0.2, 0.3, 0.4, 0.5, 0.6, 0.7, 0.8, 0.9 or 1.0 mm may be used. For a twin-screw-extruder type ZSE 18, the extrusion parameters may be adjusted e.g. to the following values: rotational speed of the screws: 120 Upm; delivery rate 2 kg/h for a ZSE 18 or 5 kg/h, 10 kg/h, or even 20 kg/h and more for a ZSE27; product temperature: in front of die 125° C. and behind die 135° C.; and jacket temperature: 110° C. The throughput can generally be increased by increasing the number of dies at the extruder outlet.

Preferably, extrusion is performed by means of twin-screw-extruders or planetary-gear-extruders, twin-screw extruders (co-rotating or contra-rotating) being particularly preferred.

The particles according to the invention are preferably produced by thermoforming with the assistance of an extruder without any observable consequent discoloration of the extrudates. The particles may be produced e.g. by means of a Micro Pelletizer (Leistritz, Nürnberg, Germany).

The process for the preparation of the particles according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the particles according to the invention can be regarded as "extruded pellets". The term "extruded pellets" has structural implications which are understood by persons skilled in the art. A person skilled in the art knows that pelletized dosage forms can be prepared by a number of techniques, including:

drug layering on nonpareil sugar or microcrystalline cellulose beads,
spray drying,
spray congealing,
rotogranulation,
hot-melt extrusion,
spheronization of low melting materials, or
extrusion-spheronization of a wet mass.

Accordingly, "extruded pellets" can be obtained either by hot-melt extrusion or by extrusion-spheronization.

"Extruded pellets" can be distinguished from other types of pellets, as extruded pellets typically have a different shape. The shape of the extruded pellets is typically more cut-rod-like than perfectly globated round.

"Extruded pellets" can be distinguished from other types of pellets because they are structurally different. For example, drug layering on nonpareils yields multilayered pellets having a core, whereas extrusion typically yields a monolithic mass comprising a homogeneous mixture of all ingredients. Similarly, spray drying and spray congealing typically yield spheres, whereas extrusion typically yields cylindrical extrudates which can be subsequently spheronized.

The structural differences between "extruded pellets" and "agglomerated pellets" are significant because they may affect the release of active substances from the pellets and consequently result in different pharmacological profiles. Therefore, a person skilled in the pharmaceutical formulation art would not consider "extruded pellets" to be equivalent to "agglomerated pellets".

The pharmaceutical dosage forms according to the invention may be prepared by any conventional method. Preferably, however, the pharmaceutical dosage forms are prepared by compression. Thus, particles as hereinbefore defined are preferably mixed, e.g. blended and/or granulated (e.g. wet granulated), with matrix material and the resulting mix (e.g. blend or granulate) is then compressed, preferably in moulds, to form pharmaceutical dosage forms. It is also envisaged that the particles herein described may be incorporated into a matrix using other processes, such as by melt granulation (e.g. using fatty alcohols and/or water-soluble waxes and/or water-insoluble waxes) or high shear granulation, followed by compression.

When the pharmaceutical dosage forms according to the invention are manufactured by means of an eccentric press, the compression force is preferably within the range of from 5 to 15 kN. When the pharmaceutical dosage forms according to the invention are manufactured by means of a rotating press, the compression force is preferably within the range of from 5 to 40 kN, in certain embodiments>25 kN, in other embodiments 13 kN.

The pharmaceutical dosage forms according to the invention may optionally comprise a coating, e.g. a cosmetic coating. The coating is preferably applied after formation of the pharmaceutical dosage form. The coating may be applied prior to or after the curing process. Preferred coatings are Opadry® coatings available from Colorcon. Other preferred coating are Opaglos® coatings, also commercially available from Colorcon.

The pharmaceutical dosage form according to the invention is characterized by excellent storage stability. Preferably, after storage for 6 months, 3 months, 2 months, or 4 weeks at 40° C. and 75% rel. humidity, the content of pharmacologically active compound amounts to at least 98.0%, more preferably at least 98.5%, still more preferably at least 99.0%, yet more preferably at least 99.2%, most preferably at least 99.4% and in particular at least 99.6%, of its original content before storage. Suitable methods for measuring the content of the pharmacologically active compound in the pharmaceutical dosage form are known to the skilled artisan. In this regard it is referred to the Eur. Ph. or the USP, especially to reversed phase HPLC analysis. Preferably, the pharmaceutical dosage form is stored in closed, preferably sealed containers.

The particles and pharmaceutical dosage forms according to the invention may be used in medicine, e.g. as an analgesic. The particles and pharmaceutical dosage forms are therefore particularly suitable for the treatment or management of pain. In such pharmaceutical dosage forms, the pharmacologically active compound is preferably an analgesic.

A further aspect according to the invention relates to the pharmaceutical dosage form as described above for use in the treatment of pain.

A further aspect according to the invention relates to the use of a pharmaceutical dosage form as described above for avoiding or hindering the abuse of the pharmacologically active compound contained therein.

A further aspect according to the invention relates to the use of a pharmaceutical dosage form as described above for avoiding or hindering the unintentional overdose of the pharmacologically active compound contained therein.

In this regard, the invention also relates to the use of a pharmacologically active compound as described above and/or a polyalkylene oxide as described above for the manufacture of the pharmaceutical dosage form according to the invention for the prophylaxis and/or the treatment of a disorder, thereby preventing an overdose of the pharmacologically active compound, particularly due to comminution of the pharmaceutical dosage form by mechanical action.

The following examples further illustrate the invention but are not to be construed as limiting its scope.

General Operation Procedures

Powder mixtures of various ingredients were manufactured by weighing (10 kg balance), sieving (1.0 mm hand sieve) and blending. The thus obtained powder mixtures were then hot-melt extruded (twin-screw extruder, Leistritz ZSE 18, blunt ends of kneading elements, and extrusion diameter of 8×0.8 mm). The extrudates were pelletized (LMP) and then analyzed.

In vitro dissolution was tested in accordance with USP (apparatus II), in 600 ml 0.1 M HCl (pH 1) at 75 rpm (n=3).

Resistance against solvent extraction was tested by dispensing particles in 5 ml of boiling water. After boiling for 5 minutes the liquid was drawn up into a syringe (needle 21G equipped with a cigarette filter), and the amount of the pharmacologically active ingredient contained in the liquid within the syringe was determined via HPLC.

The test was performed on the extrudates as such but not on capsules or tablets containing such extrudates, as this test more relevant with respect to drug abuse. The other constituents of dosage forms (e.g. capsules or tablets) typically make it even more difficult for the abuser to tamper with the dosage form, e.g. by blocking the filters of syringes and the like. Thus, in the course of tampering, abusers frequently initially separate the drug containing subunits of dosage forms (here extrudates) from the remainder of the dosage forms in order to facilitate subsequent abuse, e.g. by extraction. Accordingly, it is more significant to evaluate tamper resistance of the extrudates instead of the overall dosage forms.

EXAMPLE 1—OXYCODONE

Powder mixtures of the following ingredients were manufactured and subsequently hot-melt extruded under the following extrusion conditions:

| per dosis | 1-1 mg/wt.-% | 1-2 mg/wt.-% | 1-3 mg/wt.-% | 1-4 mg/wt.-% | 1-5 mg/wt.-% |
|---|---|---|---|---|---|
| Oxycodone HCl | 10.00/5.56 | 10.00/5.56 | 10.00/5.56 | 10.00/5.56 | 10.00/5.56 |
| Citric acid | 1.44/0.80 | 1.44/0.80 | 1.44/0.80 | 1.44/0.80 | 1.44/0.80 |
| Macrogol 6000 | 25.20/14.00 | 25.20/14.00 | 25.20/14.00 | 25.20/14.00 | 25.20/14.00 |
| α-Tocopherol | 0.36/0.20 | 0.36/0.20 | 0.36/0.20 | 0.36/0.20 | 0.36/0.20 |
| Xanthan Gum Type 602 | 9.00/5.00 | 9.00/5.00 | 9.00/5.00 | 9.00/5.00 | 9.00/5.00 |
| Polyethylene oxide 7 Mio. | 98.00/54.44 | 98.00/54.44 | 98.00/54.44 | 98.00/54.44 | 95.22/52.20 |
| Sodium bicarbonate | — | — | — | — | 2.78/1.54 |
| Sodium starch glycolate | 36.00/20.00 | — | — | — | — |
| Croscarmellose sodium | — | 36.00/20.00 | — | — | — |
| Starch 1500 | — | — | 36.00/20.00 | — | — |
| Maize starch | — | — | — | 36.00/20.00 | — |
| Carbomer Carbopol 71G | — | — | — | — | 36.00/20.00 |
| Σ | 180.00/100.00 | 180.00/100.00 | 180.00/100.00 | 180.00/100.00 | 180.00/100.00 |
| Speed screw [rpm] | 100 | 100 | 100 | 100 | 120 |
| Feed rate [g/min] | 16.66 | 16.66 | 16.66 | 16.66 | 16.66 |
| Melt pressure [bar] | 119 | 141 | 136 | 135 | 116 |
| melt temperature discharge [° C.] | 140 | 143 | 142 | 143 | 145 |

The in vitro dissolution test revealed the following release profiles:

| | Dissolution Oxycodone % | | | | |
|---|---|---|---|---|---|
| | 1-1 | 1-2 | 1-3 | 1-4 | 1-5 |
| after 5 min | 70 | 74 | 66 | 78 | 58 |
| after 15 min | 88 | 91 | 88 | 94 | 83 |
| after 30 min | 94 | 94 | 95 | 100 | 92 |
| after 60 min | 96 | 96 | 97 | 102 | 96 |

The test for tamper-resistance provided the following results (where all tested pellets remained intact after the breaking strength tester had reached its upper force limit):

| test battery | 1-1 | 1-2 | 1-3 | 1-4 | 1-5 |
|---|---|---|---|---|---|
| 1 | 0.00* | 1.34 | 0.00* | 22.40 | 0.00* |
| 2 | 0.00* | 3.07 | 20.20 | 30.32 | 0.00* |
| 3 | 0.00* | 1.26 | 6.03 | 18.67 | 0.00* |
| mean [%] | 0.00* | 1.89 | 8.74 | 28.80 | 0.00* |
| SD [%] | 0.00* | 1.02 | 10.37 | 5.95 | 0.00* |

*not tested, sample too jelly and could not be drawn into syringe

It becomes clear from the above experimental data that as far as tamper-resistant dosage forms providing immediate release are concerned, the tested disintegrants provide different performance. Under the given experimental conditions, cellulose derivatives (e.g. croscarmellose sodium) provided the best performance, followed by starch derivatives (e.g. sodium starch glycolate) and gas releasing substances (here sodium bicarbonate), followed by pregelatinized starch (e.g. starch 1500) and standard starch (e.g. native maize starch).

EXAMPLE 2—HYDROCODONE

Powder mixtures of the following ingredients were manufactured and subsequently hot-melt extruded under the following extrusion conditions:

| per dosis | 2-1 mg/wt.-% | 2-2 mg/wt.-% |
|---|---|---|
| Hydrocodone bitartrate | 10.00/5.56 | 10.00/5.56 |
| Citric acid | 1.44/0.80 | 1.44/0.80 |
| Macrogol 6000 | 25.20/14.00 | 25.20/14.00 |
| α-Tocopherol | 0.36/0.20 | 0.36/0.20 |
| Xanthan Gum Type 602 | 9.00/5.00 | 9.00/5.00 |
| Polyethylene oxide 7 Mio. | 98.00/54.44 | 98.00/54.44 |
| Carboxymethyl starch | 36.00/20.00 | — |
| Croscarmellose sodium | — | 36.00/20.00 |
| Σ | 180.00/100.00 | 180.00/100.00 |
| Speed screw [rpm] | 100 | 100 |
| Feed rate [g/min] | 16.66 | 16.66 |
| Melt pressure [bar] | 132 | 157 |
| melt temperature discharge [° C.] | 143 | 143 |

The in vitro dissolution test revealed the following release profiles:

| | Dissolution Hydrocodone % | |
|---|---|---|
| | 2-1 | 2-2 |
| after 5 min | 73 | 81 |
| after 15 min | 87 | 98 |
| after 30 min | 92 | 102 |
| after 60 min | 94 | 104 |

The test for tamper-resistance provided the following results (where all tested pellets remained intact after the breaking strength tester had reached its upper force limit):

| test battery | 2-1 | 2-2 |
|---|---|---|
| 1 | 8.79 | 0.00* |
| 2 | 4.75 | 1.09 |
| 3 | 2.78 | 1.70 |
| mean [%] | 5.44 | 0.93 |
| SD [%] | 3.06 | 0.86 |

*not tested, sample too jelly and could not be drawn into syringe

EXAMPLE 3—HYDROMORPHONE

Powder mixtures of the following ingredients were manufactured and subsequently hot-melt extruded under the following extrusion conditions:

| per dosis | 3-1 mg/wt.-% | 3-2 mg/wt.-% |
|---|---|---|
| Hydromorphone HCl | 8.00/5.33 | 8.00/5.33 |
| Citric acid | 1.20/0.80 | 1.20/0.80 |
| Macrogol 6000 | 15.00/10.00 | 15.00/10.00 |
| α-Tocopherol | 0.30/0.20 | 0.30/0.20 |
| Xanthan Gum Type 602 | 7.50/5.00 | 7.50/5.00 |
| Polyethylene oxide 7 Mio. | 88.00/58.67 | 88.00/58.67 |
| Carboxymethyl starch | 30.00/20.00 | — |
| Croscarmellose sodium | — | 36.00/20.00 |
| Σ | 150.00/100.00 | 150.00/100.00 |
| Speed screw [rpm] | 100 | 100 |
| Feed rate [g/min] | 16.66 | 16.66 |
| Melt pressure [bar] | 94 | 159 |
| melt temperature discharge [° C.] | 146 | 145 |

The in vitro dissolution test revealed the following release profiles:

| | Dissolution Hydromorphone % | |
|---|---|---|
| | 3-1 | 3-2 |
| after 5 min | 51 | 43 |
| after 15 min | 81 | 78 |
| after 30 min | 91 | 91 |
| after 60 min | 93 | 94 |

The test for tamper-resistance provided the following results (where all tested pellets remained intact after the breaking strength tester had reached its upper force limit):

| test battery | 3-1 | 3-2 |
|---|---|---|
| 1 | 22.89 | 12.25 |
| 2 | 18.18 | 4.47 |
| 3 | 0.00* | 3.10 |
| mean [%] | 13.69 | 6.61 |
| SD [%] | 12.09 | 4.94 |

*not tested, sample too jelly and could not be drawn into syringe

EXAMPLE 4—MORPHINE

Powder mixtures of the following ingredients were manufactures and subsequently hot-melt extruded under the following extrusion conditions:

| per dosis | 4-1 mg/wt.-% | 4-2 mg/wt.-% |
|---|---|---|
| Morphine sulfate•5 H$_2$O | 10.00/5.56 | 10.00/5.56 |
| Citric acid | 1.44/0.80 | 1.44/0.80 |
| Macrogol 6000 | 25.20/14.00 | 25.20/14.00 |
| α-Tocopherol | 0.36/0.20 | 0.36/0.20 |
| Xanthan Gum Type 602 | 9.00/5.00 | 9.00/5.00 |
| Polyethylene oxide 7 Mio. | 98.00/54.44 | 98.00/54.44 |
| Carboxymethyl starch | 36.00/20.00 | — |
| Croscarmellose sodium | — | 36.00/20.00 |
| Σ | 180.00/100.00 | 180.00/100.00 |
| Speed screw [rpm] | 100 | * |
| Feed rate [g/min] | 16.66 | |
| Melt pressure [bar] | 181 | |
| melt temperature discharge [° C.] | 143 | |

* could not be extruded under the given conditions; stronger equipment or higher temperatures needed The in vitro dissolution test revealed the following release profile:

|  | Dissolution Morphine sulfate % 4-1 |
| --- | --- |
| after 5 min | 58 |
| after 15 min | 83 |
| after 30 min | 90 |
| after 60 min | 91 |

The test for tamper-resistance provided the following results (where all tested pellets remained intact after the breaking strength tester had reached its upper force limit):

| test battery | 4-1 |
| --- | --- |
| 1 | 0.00* |
| 2 | 0.00* |
| 3 | 0.00* |
| mean [%] | 0.00* |
| SD [%] | 0.00* |

*not tested, sample too jelly and could not be drawn into syringe

EXAMPLE 5—AMPHETAMINE SULFATE

Powder mixtures of the following ingredients were manufactured and subsequently hot-melt extruded under the following extrusion conditions:

| per dosis | 5-1 mg/wt.-% | 5-2 mg/wt.-% | 5-3 mg/wt.-% | 5-4 mg/wt.-% |
| --- | --- | --- | --- | --- |
| Amphetamine sulfate | 30.00/12.00 | 30.00/12.00 | 30.00/12.00 | 30.00/12.00 |
| Citric acid | 2.00/0.80 | 2.00/0.80 | — | — |
| PEG 6000 | 35.00/14.00 | 35.00/14.00 | 32.60/13.00 | 32.60/13.00 |
| α-Tocopherol | 0.50/0.20 | 0.50/0.20 | 0.50/0.20 | 0.50/0.20 |
| Xanthan Gum Type 602 | — | 12.50/5.00 | — | — |
| Polyethylene oxide 7 Mio. | 182.50/73.00 | 120.00/48.00 | 136.90/54.70 | 136.90/54.70 |
| Sodium hydrogen carbonate | — | — | — | — |
| Croscarmellose sodium | — | 50/20.00 | 50.00/20.00 | — |
| Starch 1500 | — | — | — | — |
| Carboxymethyl starch | — | — | — | 50.00/20.00 |
| PVP-CL | — | — | — | — |
| Σ | 250.00/100.00 | 250.00/100.00 | 250.0/100.00 | 250.0/100.00 |
| Speed screw [rpm] | 100 | 100 | 100 | 100 |
| Extruder Load [%] | 75.00 | 75.00 | 75.00 | 75.00 |
| Melt pressure [bar] | 1 | 1 | 1 | 1 |
| melt temperature discharge [° C.] | 145 | 145 | 145 | 145 |

| per dosis | 5-5 mg/wt.-% | 5-6 mg/wt.-% | 5-7 mg/wt.-% |
| --- | --- | --- | --- |
| Amphetamine sulfate | 30.00/12.00 | 30.00/12.00 | 30.00/12.00 |
| Citric acid | — | — | — |
| PEG 6000 | 32.60/13.00 | 32.60/13.00 | 32.60/13.04 |
| α-Tocopherol | 0.50/0.20 | 0.50/0.20 | 0.50/0.20 |
| Xanthan Gum Type 602 | — | — | — |
| Polyethylene oxide 7 Mio. | 136.90/54.70 | 136.90/54.70 | 136.90/54.76 |
| Sodium hydrogen carbonate | — | 50.00/20.00 | — |
| Croscarmellose sodium | — | — | — |
| Starch 1500 | 50.00/20.00 | — | — |
| Carboxymethyl starch | — | — | — |
| PVP-CL | — | — | 50.00/20.00 |
| Σ | 250.0/100.00 | 250.0/100.00 | 250.00/100.00 |
| Speed screw [rpm] | 100 | 100 | 100 |
| Extruder Load [%] | 75.00 | 75.00 | 75.00 |
| Melt pressure [bar] | 1 | 1 | 1 |
| melt temperature discharge [° C.] | 145 | 145 | 145 |

The in vitro dissolution test revealed the following release profiles:

| Dissolution Amphetamine sulfate % | 5-1 | 5-2 | 5-3 | 5-4 | 5-5 | 5-6 | 5-7 |
| --- | --- | --- | --- | --- | --- | --- | --- |
| after 5 min | 67 | 61 | 51 | 48 | 62 | 45 | 63 |
| after 15 min | 90 | 90 | 85 | 81 | 83 | 70 | 87 |
| after 30 min | 96 | 97 | 94 | 93 | 94 | 80 | 93 |
| after 60 min | 98 | 99 | 97 | 97 | 98 | 84 | 96 |

The test for tamper-resistance provided the following results (where all tested pellets remained intact after the breaking strength tester had reached its upper force limit):

| test battery | 5-1 | 5-2 | 5-3 | 5-4 | 5-5 | 5-6 | 5-7 |
| --- | --- | --- | --- | --- | --- | --- | --- |
| 1 | 38.41 | 32.54 | 6.11 | 11.31 | 4.57 | 8.23 | 44.80 |
| 2 | 28.83 | 33.63 | 11.43 | 8.18 | 0.00* | 8.61 | 51.17 |
| 3 | 23.67 | 12.16 | 14.56 | 5.20 | 0.00* | 12.77 | 50.96 |
| mean [%] | 30.30 | 26.11 | 10.70 | 8.23 | 0.00* | 9.87 | 48.98 |
| SD [%] | 7.48 | 12.09 | 4.27 | 3.06 | 0.00* | 2.52 | 3.62 |

*not tested, sample too jelly and could not be drawn into syringe

It becomes clear from the above experimental data that as far as tamper-resistant dosage forms providing immediate release are concerned, the tested disintegrants provide an improved resistance against solvent extraction. Croscarmellose sodium (5-2, 5-3), carboxymethyl starch (5-4), starch 1500 (5-5) and sodium hydrogen carbonate provided the best results, whereas PVP-CL (5-7) did not show an advantage over the comparative composition (5-1).

EXAMPLE 6—GELLING AGENT AND DISINTEGRANT

The influence of the presence and absence of gelling agent as well as the influence of the presence and absence of disintegrant was investigated in analogy to Examples 1 to 5. The following compositions A to F were each prepared for Oxycodone, Hydrocodone, Morphine sulfate and Hydromorphone, respectively:

| Substance | 6-A mg | 6-A wt.-% | 6-B mg | 6-B wt.-% | 6-C mg | 6-C wt.-% | 6-D mg | 6-D wt.-% | 6-E mg | 6-E wt.-% | 6-F mg | 6-F wt.-% |
|---|---|---|---|---|---|---|---|---|---|---|---|---|
| API[1] | 10.00 | 5.56 | 10.00 | 5.56 | 10.00 | 5.56 | 10.00 | 5.56 | 10.00 | 5.56 | 10.00 | 5.56 |
| Citric acid | 1.44 | 0.80 | 1.44 | 0.80 | 1.44 | 0.80 | 1.44 | 0.80 | 1.44 | 0.80 | 1.44 | 0.80 |
| PEG | 25.20 | 14.00 | 25.20 | 14.00 | 25.20 | 14.00 | 25.20 | 14.00 | 25.20 | 14.00 | 25.20 | 14.00 |
| α-Toc. | 0.36 | 0.20 | 0.36 | 0.20 | 0.36 | 0.20 | 0.36 | 0.20 | 0.36 | 0.20 | 0.36 | 0.20 |
| PEO | 143.0 | 79.44 | 107.0 | 59.44 | 107.0 | 59.44 | 134.0 | 74.44 | 98.00 | 54.44 | 98.00 | 54.44 |
| Carbopol | — | — | 36.00 | 20.00 | 27.00 | 15.00 | — | — | — | — | — | — |
| Xanthan | — | — | — | — | 9.00 | 5.00 | 9.00 | 5.00 | 9.00 | 5.00 | 9.00 | 5.00 |
| Carb.MS | — | — | — | — | — | — | — | — | 36.00 | 20.00 | — | — |
| CrosCS | — | — | — | — | — | — | — | — | — | — | 36.00 | 20.00 |
| Σ | 180 | 100 | 180 | 100 | 180 | 100 | 180 | 100 | 180 | 100 | 180 | 100 |

[1]The compositions A to F containing Hydromorphone as API were modified in that they contained 8.00 mg Hydromorphone only. The difference of 2.00 mg was replaced by the corresponding amount of PEO
API = pharmacologically active ingredient;
PEG = Polyethylene glycol 6000;
α-Toc. = α-Tocopherole;
PEO = polyethylene oxide 7 Mio;
Carbopol = Carbopol 71G;
Xanthan = Xanthan gum;
Carb. MS = Carboxy methyl starch;
CrosCS = Croscarmellose sodium In vitro release as well as resistance against solvent extraction were determined in accordance with the invention. The results for the different pharmacologically active ingredients are shown in the table here below:

| Formulation | Oxycodone extract. | Oxycodone diss. | Hydrocodone extract. | Hydrocodone diss. | Morphine sulfate extract. | Morphine sulfate diss. | Hydromorphone extract. | Hydromorphone diss. |
|---|---|---|---|---|---|---|---|---|
| 6-A | 50% | 73% | 40% | 87% | 34% | 87% | 49% | 84% |
| 6-B | 40% | 90% | 0% | 91% | 9% | 83% | 29% | 87% |
| 6-C | 28% | 90% | 0% | 95% | 3% | 82% | 26% | 89% |
| 6-D | 12% | 91% | 32% | 75% | 14% | 88% | 33% | 91% |
| 6-E | 0% | 94% | 5% | 92% | 0% | 90% | 14% | 91% |
| 6-F | 2% | 94% | 1% | 103% | — | — | 7% | 91% | extract. = extracted in solvent;
diss = dissolution after 30 minutes

It becomes clear from the above comparative data that the disintegrants in inventive formulations E and F in accordance with the present invention provide best performance with respect to immediate drug release and resistance against solvent extraction for all tested pharmacologically active ingredients, whereas the comparative formulations A, B, C and D only provided partial effects for some of the tested pharmacologically active ingredients.

EXAMPLE 7—QUANTITY OF DISINTEGRANT PART I

The influence of the content of disintegrant was investigated in analogy to Examples 1 to 6. Compositions 7-1 to 7-3 were prepared and in vitro dissolution as well as resistance against solvent extraction were determined.

| Substance per dose | 7-1 mg | 7-1 wt.-% | 7-2 mg | 7-2 wt.-% | 7-3 mg | 7-3 wt.-% |
|---|---|---|---|---|---|---|
| Oxycodone HCl | 10.00 | 5.56 | 10.00 | 5.56 | 10.00 | 5.56 |
| Citric acid | 1.44 | 0.80 | 1.44 | 0.80 | 1.44 | 0.80 |

-continued

| Substance per dose | 7-1 mg | 7-1 wt.-% | 7-2 mg | 7-2 wt.-% | 7-3 mg | 7-3 wt.-% |
|---|---|---|---|---|---|---|
| PEG 6000 | 27.51 | 15.28 | 25.20 | 14.00 | 27.51 | 15.28 |
| α-Tocopherol | 0.36 | 0.20 | 0.36 | 0.20 | 0.36 | 0.20 |
| Xanthan Gum Type 602 | 9.00 | 5.00 | 9.00 | 5.00 | 9.00 | 5.00 |

-continued

| Substance | 7-1 | | 7-2 | | 7-3 | |
|---|---|---|---|---|---|---|
| per dose | mg | wt.-% | mg | wt.-% | mg | wt.-% |
| PEO 7 Mio. | 104.69 | 58.16 | 98.00 | 54.44 | 91.31 | 50.73 |
| Sodium starch glycolate | 27.00 | 15.00 | 36.00 | 20.00 | 45.00 | 25.00 |
| | 180.00 | 100.00 | 180.00 | 100.00 | 180.00 | 100.00 |
| Dissolution (n = 3): | | | | | | |
| 0 | | 0.00 | | 0.00 | | 0.00 |
| 5 | | 64.46 | | 69.73 | | 62.04 |
| 15 | | 78.42 | | 87.57 | | 81.83 |
| 30 | | 91.24 | | 94.44 | | 91.76 |
| 60 | | 94.82 | | 96.49 | | 95.12 |
| extraction without milling: | | | | | | |
| mean [%] | | 10.10 | | 0.00* | | 16.37 |
| SD [%] | | 4.67 | | 0.00* | | 12.67 |

*not tested, sample too jelly and could not be drawn into syringe

It becomes clear from the above comparative data that under the given conditions the best results could be achieved at a content of 20 wt.-% disintegrant (here sodium starch glycolate).

EXAMPLE 8—QUANTITY OF DISINTEGRANT PART II

The influence of the content of disintegrant was investigated in analogy to Examples 1 to 7. Compositions 8-1 to 8-4 were prepared and in vitro dissolution as well as resistance against solvent extraction were determined.

| | 8-1 | | 8-2 | | 8-3 | | 8-4 | |
|---|---|---|---|---|---|---|---|---|
| per dose | mg | wt.-% | mg | wt.-% | mg | wt.-% | mg | wt.-% |
| Amphetamine sulfate | 30.00 | 13.95 | 30.00 | 16.67 | 30.00 | 13.95 | 30.00 | 16.67 |
| PEG 6000 | 27.20 | 12.65 | 21.85 | 12.14 | 27.20 | 12.65 | 21.85 | 12.14 |
| α-Tocopherol | 0.43 | 0.20 | 0.36 | 0.20 | 0.43 | 0.20 | 0.36 | 0.20 |
| Polyethylene oxide 7 Mio. | 114.37 | 53.20 | 91.79 | 50.99 | 114.37 | 53.20 | 91.79 | 50.99 |
| Croscarmellose sodium | 43.00 | 20.00 | 36.00 | 20.00 | | | | |
| Starch 1500 | | | | | 43.00 | 20.00 | 36.00 | 20.00 |
| Σ | 215.00 | 100.00 | 180.00 | 100.00 | 215.00 | 100.00 | 180.00 | 100.00 |
| Speed screw [rpm] | 100 | | 100 | | 100 | | 100 | |
| Extruder Load [%] | 75.00 | | 75.00 | | 75.00 | | 75.00 | |
| Melt pressure [bar] | 1 | | 1 | | 1 | | 1 | |
| melt temperature discharge [° C.] | 145 | | 145 | | 145 | | 145 | |

The in vitro dissolution test revealed the following release profiles:

| | Dissolution Amphetamine sulfate % | | | |
|---|---|---|---|---|
| | 8-1 | 8-2 | 8-3 | 8-4 |
| after 5 min | 60 | 74 | 75 | 78 |
| after 15 min | 91 | 94 | 82 | 81 |
| after 30 min | 97 | 99 | 84 | 87 |
| after 60 min | 97 | 99 | 85 | 88 |

The test for tamper-resistance provided the following results (where all tested pellets remained intact after the breaking strength tester had reached its upper force limit):

| test battery | 8-1 | 8-2 | 8-3 | 8-4 |
|---|---|---|---|---|
| 1 | 7.92 | 17.51 | 0.00* | 6.42 |
| 2 | 7.74 | 12.79 | 0.00* | 3.66 |
| 3 | 8.49 | 16.85 | 0.00* | 1.83 |
| mean [%] | 8.05 | 15.72 | 0.00* | 3.97 |
| SD [%] | 0.39 | 2.56 | 0.00* | 2.31 |

*not tested, sample too jelly and could not be drawn into syringe

It becomes clear from the above comparative data that under the given conditions lower contents of disintegrant provide an improved resistance against solvent extraction.

EXAMPLE 9—TABLETS CONTAINING PELLETS 8-1 AND 8-4

Tablets containing pellets 8-1 and 8-4 were prepared:

| per tablet [mg] | per tablet [mg] | Excipients | [%] | Form |
|---|---|---|---|---|
| 215.00 | 30.00 | Amfetamine Sulfate | 30.71 | Pellets |
| | 114.37 | Polyethylenoxid 7 Mio. | | |
| | 27.20 | Macrogol 6000 | | |
| | 0.43 | Alpha-Tocopherol | | |
| | 43.00 | Croscarmellose Sodium | | |
| 485.00 | | Microcrystalline Cellulose | 69.29 | Powder Mix |

-continued

| per tablet [mg] | per tablet [mg] | Excipients | [%] | Form |
|---|---|---|---|---|
| | | Crospovidone Magnesiumstearate Ph. Eur. | | |
| 700.0 | 700.0 | — | 100.00 | — |
| 180 | 30.00 | Amfetamine Sulfate | 25.71 | Pellets |
| | 91.79 | Polyethylenoxid 7 Mio. | | |
| | 21.85 | Macrogol 6000 | | |
| | 0.36 | Alpha-Tocopherol | | |
| | 36.0 | Starch 1500 | | |

-continued

| per tablet [mg] | per tablet [mg] | Excipients | [%] | Form |
|---|---|---|---|---|
| | 520.00 | Microcrystalline Cellulose Crospovidone Magnesiumstearate Ph. Eur. | 74.29 | Powder Mix |
| 700.0 | 700.0 | — | 100.00 | — |

The test for tamper-resistance of pulverized pellets and pulverized tablets provided the following results:

| test battery | Tablet containing pellets 8-1 | Tablet containing pellets 8-4 |
|---|---|---|
| 1 | 2.27 | 0.00* |
| 2 | 2.48 | 0.00* |
| 3 | 0.00* | 0.00* |
| mean [%] | 0.00* | 0.00* |
| SD [%] | 0.00* | 0.00* |

*not tested, sample too jelly and could not be drawn into syringe

It becomes clear from the above comparative data that under the given conditions tablets containing pellets provide an improved resistance against solvent extraction compared to pellets alone.

EXAMPLE 10—OXYCODONE PELLETS AND TABLETS CONTAINING OXYCODONE PELLETS

Powder mixtures of the following ingredients were manufactured and subsequently hot-melt extruded:

| per dosis | 10-1 mg/wt.-% |
|---|---|
| Oxycodone HCl | 30.00/12.00 |
| Citric acid | 1.25/0.50 |
| α-Tocopherol | 0.50/0.20 |
| Polyethylene oxide 7 Mio. | 133.25/53.30 |
| Macrogol 6000 | 35.00/14.00 |
| Carbopol 71G | 50.00/20.00 |
| Σ | 250.00/100.00 |

Tablets containing oxycodone pellets were prepared:

| Excipients | per tablet [mg]/ | [wt.-%] |
|---|---|---|
| Oxycodone pellets | 250.00 | 50.00 |
| Avicel PH101/PVP-CL Aerosil 200 Mg stearate | 250.00 | 50.00 |
| Σ | 500.00 | 100.00 |

The test for tamper-resistance of intact tablets and intact pellets provided the following results:

| test battery | Oxycodone pellets | Tablet containing oxycodone pellets |
|---|---|---|
| 1 | 47.10 | 30.90 |
| 2 | 46.82 | 27.97 |
| 3 | 39.68 | 27.23 |
| mean [%] | 44.53 | 28.70 |

It becomes clear from the above comparative data that under the given conditions tablets containing pellets provide an improved resistance against solvent extraction compared to pellets alone.

EXAMPLE 11—AMPHETAMINE PELLETS AND CAPSULES CONTAINING AMPHETAMINE PELLETS a) Capsules containing pellets 8-1 and 8-4 were prepared.

| Phase [mg] | Component | Amount per capsule [mg] | Amount [%] |
|---|---|---|---|
| Pellets 215.00 | Amphetamine sulfate | 30.00 | 54.43 |
| | Polyethylene oxide 7000000 | 114.37 | |
| | Macrogol 6000 | 27.20 | |
| | Alpha Tocopherol | 0.43 | |
| | Croscarmellose sodium (Vivasol ®) | 43.00 | |
| Powder blend 180.00 | Mannitol (Partek M200 ®) Colloidal silicon dioxide | 180.00 | 45.57 |
| | Sum | 395.00 mg | 100.00 |
| Pellets 180.00 | Amphetamine sulfate | 30.00 | 50.00 |
| | Polyethylene oxide 7000000 | 91.79 | |
| | Macrogol 6000 | 21.85 | |
| | Alpha Tocopherol | 0.36 | |
| | Pre-gelatinized maize starch (Starch 1500) | 36.00 | |
| Powder blend 180.00 | Mannitol (Partek M200 ®) Colloidal silicon dioxide | 180.00 | 50.00 |
| | Sum | 360.00 mg | 100.00 |

The mixtures were filled in capsules of size 0.

b) Pellets 8-4 were coated with a protective coating (Opadry clear) by means of a fluid-bed granulation process and the thus coated pellets were filled in capsules without additional constituents.

| Phase [mg] | Component | Amount per capsule [mg] | Amount [%] |
|---|---|---|---|
| Pellets 193.90 | Amphetamine sulfate | 30.00 | 100.00 |
| | Polyethylene oxide 7000000 | 91.79 | |
| | Macrogol 6000 | 21.85 | |
| | Alpha Tocopherol | 0.36 | |
| | Pre-gelatinized maize starch (Starch 1500) | 36.00 | |
| | Opadry II clear | 13.90 | |
| | Sum | 193.90 mg | 100.00 |

Figure 4:
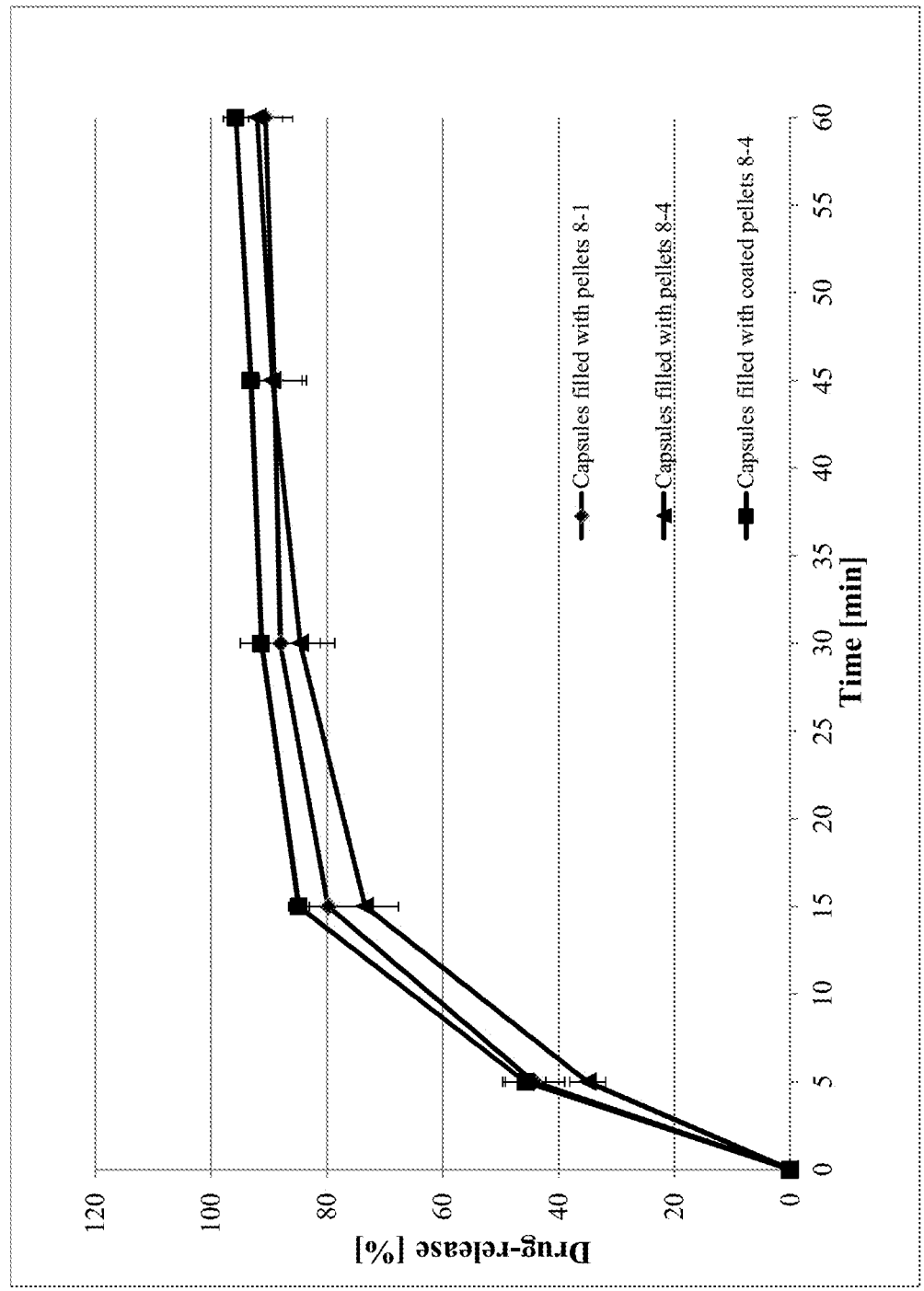
FIG. 4 provides in vitro dissolution data of capsules containing pellets.

The coated pellets were filled in capsules of size 0.
The in vitro release profiles of all three capsules is shown in FIG. 4.

The invention claimed is:
1. A tamper-resistant pharmaceutical dosage form comprising a multitude of particles which comprise a pharmacologically active compound, a polyalkylene oxide, and a disintegrant;

wherein the pharmacologically active compound is a stimulant selected from the group consisting of phenylethylamine derivatives;

wherein the pharmacologically active compound is dispersed in a matrix comprising the polyalkylene oxide and the disintegrant;

wherein the disintegrant is selected from the group consisting of croscarmellose sodium, partially pre-gelatinized starch, carboxylmethyl starch, and mixtures thereof;

wherein the content of the disintegrant is 15±5.5 wt.-%, based on the total weight of the pharmaceutical dosage form and/or based on the total weight of the particles;

wherein the content of the polyalkylene oxide is at least 25 wt.-%, based on the total weight of the pharmaceutical dosage form and/or based on the total weight of the particles;

wherein the dosage form provides under in vitro conditions immediate release of the pharmacologically active compound in accordance with Ph. Eur;

wherein the particles exhibit an increased resistance against solvent extraction compared to comparison particles that are otherwise identical to said particles except the comparison particles lack any content of any disintegrant; and wherein the increased resistance against solvent extraction is determined by (a) dispensing the particles or the comparison particles in 5 ml of boiling water to form a liquid, (b) after five minutes drawing the liquid up into a syringe needle 21G equipped with a cigarette filter, and (c) determining the amount of the pharmacologically active ingredient in the liquid in the syringe by high performance liquid chromatography, wherein the increased resistance against solvent extraction compared to the comparison particles is proven by a lower amount of the pharmacologically active ingredient in the syringe in the case of the particles compared to the amount of the pharmacologically active ingredient in the syringe in the case of the comparison particles.

2. The pharmaceutical dosage form according to claim 1, wherein the stimulant is selected from the group consisting of methylphenidate, dexmethylphenidate, and the physiologically acceptable salts thereof.

3. The pharmaceutical dosage form according to claim 1, wherein the stimulant is selected from the group consisting of pseudoephedrine, and the physiologically acceptable salts thereof.

4. The pharmaceutical dosage form according to claim 1, which has a breaking strength of at least 300 N.

5. The pharmaceutical dosage form according to claim 1, which exhibits resistance against solvent extraction such that when
(i) dispensing the pharmaceutical dosage form that is either intact or has been manually comminuted by means of two spoons in 5 ml of purified water,
(ii) heating the liquid up to its boiling point,
(iii) boiling the liquid in a covered vessel for 5 min without the addition of further purified water,
(iv) drawing up the hot liquid into a syringe, and
(v) determining the amount of the pharmacologically active compound contained in the liquid within the syringe,
the liquid part of the formulation that can be separated from the remainder by means of the syringe is not more than 10 wt.-% of the pharmacologically active compound originally contained in the dosage form.

6. The pharmaceutical dosage form according to claim 1, wherein the disintegrant is partially pregelatinized starch.

7. The pharmaceutical dosage form according to claim 1, wherein the disintegrant is sodium carboxymethyl starch.

8. The pharmaceutical dosage form according to claim 1, wherein the disintegrant is croscarmellose sodium.

9. The pharmaceutical dosage form according to claim 1, wherein the content of the disintegrant is at least 10 wt.-%, based on the total weight of the particles.

10. The pharmaceutical dosage form according to claim 1, wherein the polyalkylene oxide has a weight average molecular weight of at least 500,000 g/mol.

11. The pharmaceutical dosage form according to claim 1, which provides a release profile such that under in vitro conditions in 600 ml 0.1 M HCl (pH 1) at 75 rpm after 30 min at least 90 wt.-% of the pharmacologically active ingredient that was originally contained in the dosage form have been released.

12. The pharmaceutical dosage form according to claim 1, which additionally comprises a gelling agent.

13. The pharmaceutical dosage form according to claim 12, wherein the gelling agent is a polysaccharide; or the content of the gelling agent is at least 1.0 wt.-%, based on the total weight of the pharmaceutical dosage form and/or based on the total weight of the particles.

14. The pharmaceutical dosage form according to claim 1, wherein the stimulant is selected from the group consisting of amphetamine, dexamphetamine, methylenedioxymethamphetamine, lisdexamphetamine, methamphetamine, and the physiologically acceptable salts thereof.

15. The pharmaceutical dosage form according to claim 1, wherein the content of the pharmacologically active compound is at least 5.0 wt.-%, based on the total weight of the pharmaceutical dosage form and/or based on the total weight of the particles.

16. The pharmaceutical dosage form according to claim 1, wherein the particles are hot melt-extruded.

17. The pharmaceutical dosage form according to claim 1, wherein the particles are film coated.

18. The pharmaceutical dosage form according to claim 1, which is a tablet or capsule.

19. The pharmaceutical dosage form according to claim 1, wherein the content of the polyalkylene oxide is at least 40 wt.-%, based on the total weight of the particles.

20. The pharmaceutical dosage form according to claim 1, wherein all of the polyalkylene oxide that is contained in the pharmaceutical dosage form is contained in the particles.

21. The pharmaceutical dosage form according to claim 1, wherein the stimulant is the only active ingredient in the pharmaceutical dosage form.

* * * * *